US011752165B2

(12) United States Patent
Pui et al.

(10) Patent No.: US 11,752,165 B2
(45) Date of Patent: Sep. 12, 2023

(54) BASIC CHEMOTHERAPEUTIC INTRATUMOUR INJECTION FORMULATION

(71) Applicant: US NANO FOOD & DRUG, INC., New Castle, DE (US)

(72) Inventors: Hing Sang Pui, New Castle, DE (US); Yip Shu Pui, New Castle, DE (US); Yip Ching Pui, New Castle, DE (US)

(73) Assignee: US NANO FOOD & DRUG, INC, New Castle, DE (US)

( * ) Notice: Subject to any disclaimer, the term of this patent is extended or adjusted under 35 U.S.C. 154(b) by 18 days.

(21) Appl. No.: 17/218,067

(22) Filed: Mar. 30, 2021

(65) Prior Publication Data
US 2021/0315913 A1 Oct. 14, 2021

Related U.S. Application Data

(60) Provisional application No. 63/009,220, filed on Apr. 13, 2020.

(51) Int. Cl.
| | |
|---|---|
| *A61K 31/704* | (2006.01) |
| *A61K 31/166* | (2006.01) |
| *A61K 9/00* | (2006.01) |
| *A61K 9/08* | (2006.01) |
| *A61K 47/10* | (2017.01) |
| *A61K 47/12* | (2006.01) |
| *A61K 31/131* | (2006.01) |
| *A61K 31/475* | (2006.01) |
| *A61K 31/7048* | (2006.01) |
| *A61K 31/4184* | (2006.01) |
| *A61K 47/14* | (2017.01) |
| *A61K 9/107* | (2006.01) |

(52) U.S. Cl.
CPC .......... *A61K 31/704* (2013.01); *A61K 9/0019* (2013.01); *A61K 9/08* (2013.01); *A61K 9/107* (2013.01); *A61K 31/131* (2013.01); *A61K 31/166* (2013.01); *A61K 31/4184* (2013.01); *A61K 31/475* (2013.01); *A61K 31/7048* (2013.01); *A61K 47/10* (2013.01); *A61K 47/12* (2013.01); *A61K 47/14* (2013.01)

(58) Field of Classification Search
CPC .. A61K 31/704; A61K 31/131; A61K 31/166; A61K 31/4184; A61K 31/475; A61K 31/7048; A61K 9/0019; A61K 31/136; A61K 31/357; A61K 47/10; A61K 47/12; A61K 47/14; A61K 47/02; A61K 47/44; A61K 9/08; A61P 35/00
See application file for complete search history.

(56) References Cited

U.S. PATENT DOCUMENTS

| | | |
|---|---|---|
| 5,573,781 A | 11/1996 | Brown et al. |
| 5,681,846 A | 10/1997 | Trissei |
| 5,698,582 A | 12/1997 | Bastart et al. |
| 5,714,512 A | 2/1998 | Bastart et al. |
| 6,979,456 B1 | 12/2005 | Parikh et al. |
| 7,923,536 B2 | 4/2011 | Desai et al. |
| 8,710,013 B2 | 4/2014 | Demeule et al. |
| 8,940,786 B2 | 1/2015 | Nabeta |
| 9,308,195 B2 | 4/2016 | Nabeta |
| 9,345,683 B2 | 5/2016 | Khamar et al. |
| 9,351,997 B2 | 5/2016 | Bender |
| 9,636,406 B2 | 5/2017 | Bender |
| 10,391,090 B2 | 8/2019 | Baltezor et al. |
| 2002/0032171 A1 | 3/2002 | Chen et al. |
| 2003/0099674 A1 | 5/2003 | Chen |
| 2003/0203033 A1 | 10/2003 | Dang et al. |
| 2008/0090803 A1 | 4/2008 | Swindell et al. |
| 2008/0319048 A1 | 12/2008 | Palepu et al. |
| 2009/0118354 A1 | 5/2009 | Liu et al. |
| 2010/0041744 A1 | 2/2010 | Chung et al. |
| 2013/0150335 A1 | 6/2013 | Liu et al. |
| 2017/0326232 A1 | 11/2017 | Guiducci et al. |
| 2021/0113463 A1 | 4/2021 | Deschamps et al. |

FOREIGN PATENT DOCUMENTS

| | | |
|---|---|---|
| CN | 1923189 A | 3/2007 |
| CN | 102370645 B | 7/2014 |
| EP | 0 674 510 B1 | 8/1998 |
| EP | 1 348 430 A1 | 10/2003 |
| WO | WO 00/57852 | 10/2000 |

(Continued)

OTHER PUBLICATIONS

Strickley, R.G., Pharmaceutical Research, 2004, 21(2), p. 201-230. (Year: 2004).*
Swarbrick et al., Encyclopedia of pharmaceutical technology, 2002, Informa Health Care, 2nd ed., p. 918. (Year: 2002).*
Yang et al., "Percutaneous intratumoral injection of gemcitabine plus cisplatin mixed with fibrin glue for advanced pancreatic carcinoma" Case Report; Journal List Medicine (Baltimore) v.96 (37); Sep. 2017.
Silas Inman, "FDA Approves Alcohol-Free Docetaxel Formulation" from http://www.onclive.com/web-exclusives/fda-approves-alcohol-free-docetaxel-formulation; Published Monday, Dec. 28, 2015.
Kevin Bullis, "Nanospheres that target cancer cells and gradually release drugs could make treatment safer and more effective." MIT Technology Review, Single-Shot Chemo; Apr. 12, 2006.

(Continued)

*Primary Examiner* — Jonathan S Lau
(74) *Attorney, Agent, or Firm* — Davidson, Davidson & Kappel, LLC

(57) ABSTRACT

The invention is directed to an intratumor injectable formulation, a method of making the intratumor injectable formulation and a method of treating a malignant mass in a mammal by administering the injectable formulation directly into the malignant mass. The injectable intratumor formulation may be an emulsion, solution or suspension, all of which comprise a therapeutically effective amount of a basic chemotherapeutic drug dissolved or suspended in a biocompatible carrier, wherein the basic chemotherapeutic drug is an anthracycline base, a vina alkaloid base, an eribulin base or an alkylating agent base.

25 Claims, 1 Drawing Sheet

(56) References Cited

FOREIGN PATENT DOCUMENTS

| WO | WO 2010/083365 A1 | 7/2010 | |
|---|---|---|---|
| WO | WO-2016005995 A2 * | 1/2016 | ............ A61K 47/26 |
| WO | WO 2019/016138 A1 | 1/2019 | |
| WO | WO 2020/035806 A1 | 2/2020 | |

OTHER PUBLICATIONS

Sato et al., "Direct Delivery of a Cytotoxic Anticancer Agent into the Metastatic Lymph Node Using Nano/Microbubbles and Ultrasound" PLOS ONE; from https://doi.org/10.1371/journal_.pone. 0123619; Published Apr. 21, 2015.

Sagiv-Barfi et al., "Eradication of spontaneous malignancy by local immunotherapy" Science Translational Medicine; vol. 10, Issue 426; Jan. 31, 2018.

Lexie Metzler, "New IsoFlow Lateral Infusion Catheter Directly Targets Cancer Cells" from https://www.medicaldesignandoutsourcing.com. Published Oct. 14, 2016.

Matthew Contursi, "United by chance, ASU alumni and a Silicon Valley entrepreneur team up to innovate cancer treatment" The State Press. Published Oct. 16, 2016.https://www.statepress.com/staff/matthew-contursi.

Andrew Octavian Sasmita, "Why don't we directly inject drug into tumor?"; Internet Reference from https://www.researchgate.net/post/Why_dont_we_directly_inject_drug_into_tumor.

Bommareddy PK et al., "Intratumoral Approaches for the Treatment of Melanoma" Cancer J.; Jan./Feb. 2017; 23(1):40-47. Abstract only.

International Search Report and Written Opinion from corresponding PCT Application No. PCT/US19/47079 dated Nov. 6, 2019.

Tanaka K. et al., "Direct injection chemotherapy combined with arterial embolization in the treatment of liver cancers." Nihon Igaku Hoshasen Gakkai Zasshi; Mar. 25, 1992; 52(3); 408-10. Abstract Only.

Northwest Biotherapeutics, "DCVax®—Direct Phase I/II for All Types of Inoperable Solid" https://nwbio.com/devax-direct-phase-iii-for-all-types-of-inoperable-solid-tumor-cancers/.

Northwest Biotherapeutics, "A Phase I/II Clinical Trial Evaluating DCVax-Direct, Autologous Activated Dendritic Cells for Intratumoral Injection, in Patients with Solid Tumors" Study Record Details; https://clinicaltrials.gov/ct2/Show/NCT01882946?term=Northwest+Biotherapeutics&draw=2&rank=2; Posted on Jun. 21, 2013.

Tijia Chen et al., "Paclitaxel loaded phospholipid-based gel as a drug delivery system for local treatment of glioma" International Journal of Pharmaceutics 528, pp. 127-132, 2017.

Rani S. Sellers et al., "Effects of Miglyol 812 on Rats After 4 Weeks of Gavage as Compared with Methylcellulose/Twenn 80" Drug and Chemical Toxicology, 28:423-432, 2005.

Camille G. Wermuth, "Similarity in drugs: reflections on analogue design", Drug Discovery Today vol. 11, Nos. 7/8, pp. 348-354, Apr. 2006.

Mead Johnson. Taxol Injection, Oncology Products, Feb. 10, 2000; [online], Retrieved from URL: https://www.accessdata.fda.gov/drugsatfda_docs/label/2000/20262S36LBL.PDF on Jan. 22, 2021. (Year: 2000).

Xue-Jun Xia et al., "Formulation, Characterization and Hypersensitivity Evaluation of an Intravenous Emulsion Loaded with a Paclitaxel-Cholesterol Complex", Chem. Pharm. Bull. 59(3) pp. 321-326, 2011.

Stephen K. Dordunoo et al., "Solubility and stability of taxol: effects of buffers and cyclodextrins", International Journal of Pharmaceutics 133, pp. 191-201, 1996.

Bhullar et al. "Intratumoral acetic acid injection eradicates human prostate cancer tumors in a murine model" World journal of urology; vol. 31; issue 2; pp. 331-337 (2012).

Ahnfelt et al. "Lipodol-based emulsions used for transarterial chemoembolization and drug delivery: Effects of composition on stability and product quality" Journal of Drug Science and Technology; vol. 53 (2019).

International Search Report and Written Opinion from corresponding PCT Application No. PCT/US2021/25006 dated Aug. 17, 2021.

Zhu et al. "Review on the Stability Mechanism and Application of Water-in-Oil Emulsions Encapsulating Various Additives" Comprehensive Reviews in Food Science and Food Safety. vol. 18; Issue 6; pp. 1660-16752 (2019).

\* cited by examiner

Particle Sizing Systems, Inc.
Santa Barbara, Calif., USA
INTENSITY-Weighted NICOMP DISTRIBUTION Analysis (Solid Particle)
NICOMP SUMMARY:
Peak #1: Mean Diam.= 51.4 nm, S.Dev.= 4.2 nm (8.1%) Intens.= 100.0 %
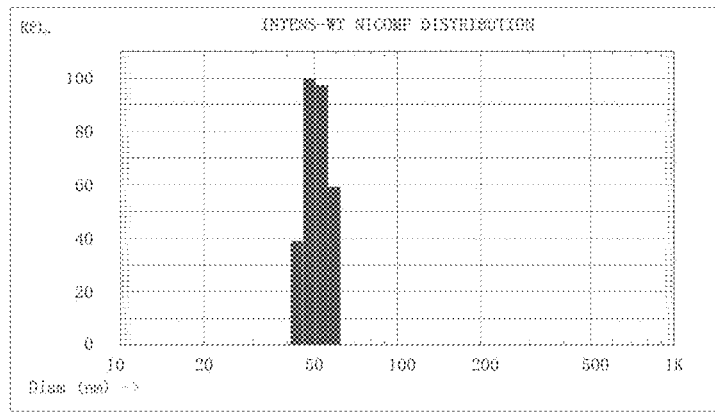

BASIC CHEMOTHERAPEUTIC INTRATUMOUR INJECTION FORMULATION

This application claims priority to U.S. Provisional Application No. 63/009,220, filed on Apr. 13, 2020; the disclosures of which are hereby incorporated by reference herein.

FIELD OF THE INVENTION

The invention is directed to pharmaceutical formulations of basic chemotherapeutic injections for use in direct injection into a malignant mass in a mammal suffering from cancer or sarcoma (e.g., human) disease and methods for production thereof.

BACKGROUND OF THE INVENTION

Cancer is a group of diseases involving abnormal cell growth with the potential to invade or spread to other parts of the body.

Cancer can spread from its original site by local spread, lymphatic spread to regional lymph nodes or by hematogenous spread via the blood to distant sites. The dispersed tumors are called metastatic tumors, while the original is called the primary tumor. Almost all cancers can metastasize and metastasis is common in the late stages of cancer and can occur via the blood or the lymphatic system or both. The typical steps in metastasis are local invasion, intravasation into the blood or lymph, circulation through the body, extravasation into the new tissue, proliferation and angiogenesis. When cancer spreads by a hematogenous route, it usually spreads all over the body. Different types of cancers tend to metastasize to particular organs, but overall, the most common places for metastases to occur are the lungs, liver, brain and the bones. Metastases are a major cause of death from cancer.

Some of the most common cancer types, such as breast cancer, cervical cancer, oral cancer, and colorectal cancer, have high cure rates when detected early and treated according to best practices. The primary goal is generally to cure cancer or to considerably prolong life. Improving the patient's quality of life is also an important goal. This can be achieved by supportive or palliative care and psychosocial support.

Cancer is often treated with some combination of radiation therapy, surgery, chemotherapy and targeted therapy (heated or cold method). Palliative care is particularly important in people with advanced disease. Surgery is a traditional approach in which all or part of a tumor is removed from the body. Surgery generally is only effective for treating the earlier stages of cancer. For more than 50% of cancer individuals, by the time they are diagnosed they are no longer candidates for effective surgical treatment. Even when surgical options are available, there is still risk as surgical procedures may increase tumor metastases through blood circulation during surgery. Most cancer patients do not die from the cancer at the time of diagnosis or surgery, but rather die from the metastasis and the recurrence of the cancer. For advanced cancer, the chance of survival is small without a new formulation and/or a new method of treatment.

Chemotherapy works by killing, stopping or slowing the growth of cancer cells, which grow and divide quickly. Chemotherapy can be used to shrink tumors that are causing pain and other problems. However, chemotherapy not only kills fast-growing cancer cells, but also kills or slows the growth of healthy cells that grow and divide quickly. As cancer cells do not have great differences from normal cells, anticancer drugs, whether given orally or by injection, can kill both cancer cells and normal cells. In fact, chemotherapy can kill more normal cells than cancer cells because there are a greater number of normal cells in the body. Examples are cells that grow and divide quickly are those that line the mouth and intestines and those that cause hair to grow. Damage to healthy cells may cause side effects, such as mouth sores, nausea, and hair loss. Such side effects often get better or go away after chemotherapy has been completed.

Other known therapies to treat cancer are also often ineffective. Radiation therapy is only effective for individuals who present with clinically localized disease at early and middle stages of cancer. Radiation is not effective for the late stages of cancer with metastasis. For advanced cancers for which surgery is no longer an option, doctors may prescribe a chemotherapeutic drug to be administered orally or by intravenous injection to eradicate the cancer cell. Chemotherapeutic drugs have been divided into water soluble drugs and water insoluble drugs. Almost all water-soluble chemotherapeutic drugs (including most anthracyclines) are acidic salts which are made by a strong acid and a weak basic chemical. All anthracycline bases, for example, are insoluble in water.

Most basic chemicals such as daunorubicin, doxorubicin, epirubicin, amrubicin, mitoxantrone, vinblastine, vincristine, vindesin, eribulin, mechlorethamine and bendamustine are unstable chemicals and are insoluble in water but are slightly soluble in an organic liquid. Therefore, most basic chemicals are reacted with an acid to form an acidic salt which is stable at room temperature, soluble in water and suitable to be made into an intravenous injection. The soluble salts available on the market are anthracycline hydrochloride, vinca alkaloids sulfate, eribulin mesylate, and nitrogen mustards hydrochloride.

Most drugs pass through the cell membrane by lipid diffusion to take effect on the cell. Most water-soluble drugs are weak acids, so the drugs exist in the form of non-dissociation type and dissociation type in solution. Only the non-dissociated drugs can dissolve into the lipid membrane and pass through the biomembrane easily due to their high lipid solubility. In contrast, dissociated drugs do not easily pass through the biomembrane due to their low lipid solubility, and as a result, they are limited to one side of the membrane, forming "ion trapping". Therefore, the degree of drug dissociation is another important factor affecting the lipid solubility and diffusion of drugs. Though some drugs are water soluble and can be made into an intravenous injection, the drug will not be able to pass through the cell membrane of the cancer cell.

The main factors affecting the lipolysis and diffusion of drugs are:
1) The area of the membrane and the concentration difference on both sides of the membrane: the larger the membrane area, the faster the diffusion; the higher the concentration on one side of the lipid membrane, the faster the diffusion speed, until the concentration on both sides of the membrane is the same, at which time, the diffusion stops.
2) Lipid solubility of the drug: In general, the larger the partition coefficient, the more the drug dissolves into the lipid membrane, the faster the diffusion. However, the drug must first be dissolved in body fluid to reach the cell membrane, so the low water content of the injection is also not conducive to the drug passing through the cell membrane.

3) Dissociation type: Only non-dissociative drugs can dissolve into the lipid membrane and pass through the biomembrane easily because of their high lipid solubility.

4) The pKa of the drug and the pH of the environment will ultimately determine the degree of drug dissociation: PKA is the negative logarithm of the dissociation constant (KA), and Ka is the pH of the solution when the drug is dissociated by 50%. Each drug has its own pKa, which is the attribute of the drug itself, and has nothing to do with the weak acid or weak base of the drug.

To facilitate the use of a water insoluble active pharmaceutical ingredient (API) in an intravenous formulation that will be injected into the blood, a medical scientist will select a water-soluble form of the API to make the intravenous formulation. Most of the chemotherapeutic drugs on the market are water soluble.

In the past, many doctors have attempted administration of anticancer drugs directly into malignant masses. However, most anticancer drugs are formulated for intravenous administration and are water soluble injections. Therefore, these drugs when injected into a malignant mass have difficulty penetrating the cell membrane. Further, water soluble anticancer drugs have difficulty staying in the interspace of cancer cells because their solubility means they will be carried away by the blood capillary of the tumor. Therefore, water-soluble anticancer drugs had little effect against the cancer cell.

Anthracyclines are made into water soluble drugs by reacting the anthracycline with hydrochloric acid, such as doxorubicin hydrochloride, epirubicin hydrochloride, amrubicin hydrochloride, mitoxantrone hydrochloride and daunorubicin hydrochloride. Water soluble anthracycline can be injected into veins or injected intra-arterially. When a water insoluble chemotherapeutic drug cannot be made into hydrochloride salt, it is instead made into an emulsion or in a formulation consisting of an excipient such as alcohol, PEG, polysorbate, albumin or a mixture thereof. These excipients make the drug soluble or dispersible in water, for example, paclitaxel albumin and paclitaxel emulsion.

Most anthracycline anticancer drugs in the market are hydrochloride salts of anthracycline including doxorubicin hydrochloride injection, epirubicin hydrochloride injection, amrubicin hydrochloride injection, mitoxantrone hydrochloride injection and daunorubicin hydrochloride injection, etc. Anthracycline hydrochlorides that are soluble in water have difficulty reaching their target cancer cells by chance because there are more normal cells than cancer cells. Water soluble anthracycline hydrochlorides also have difficulty passing through the cell membrane of cancer cells because cancer cell membranes are hydrophobic. In addition, water soluble anthracycline hydrochlorides have difficulty staying in the interspace of cancer cells because anthracycline hydrochlorides will be carried away by the blood capillary of the tumor.

In order to raise the cure rate of water-soluble anthracycline hydrochloride injections, scientists have developed different kinds of liposomes in the hope that a hydrophilic drug contained in a double lipid layer capsules can pass through the cell membrane of the cancer cell easily. Unfortunately, the result has not been good because the anthracycline hydrochloride liposome injections can enter both normal and cancer cells and can kill both normal cells and cancer cells due to the similarities between normal cells and cancer cells. Little improvement in cancer cure rate has been seen since the appearance of liposome injections onto the market, particularly because the adverse effects (e.g. the death of normal cells) prevent the patient from receiving sufficient amounts of anthracycline hydrochloride therapy. For advanced cancer, where doctors use chemotherapeutic agents to prolong life and/or improve the patient's quality of life, new formulations and new ways of treatment for the cure of cancer are still needed.

Anthracyclines are anticancer drugs that were originally derived from *Streptomyces* bacteria. Their anti-tumor activity was established in the 1960s. Anthracyclines are red aromatic polyketides and occur in a variety of forms due to the structural differences in the aglycone base molecule and the different sugar residues attached. These drugs are non-cell-cycle specific. Daunorubicin and doxorubicin were early chemotherapy agents in this class. When doctors found that tumors developed resistance to those drugs and that side effects, including cardiotoxicity, limited doses that patients could handle, medicinal chemists tried to find modifications of these drugs—analogs with wider activity and lower toxicity. More than 2000 analogs have been studied over the years in an effort to find better anthracyclines. However, only very few anthracycline analogs like epirubicin and idarubicin have been approved for clinical use. Cardiac toxicity remains a major concern when using anthracyclines intravenously.

Daunorubicin hydrochloride is the hydrochloride salt of daunorubicin which was produced by a strain of *Streptomyces coeruleorubidus*. Daunorubicin hydrochloride is soluble in water. Its molecular formula is $C_{27}H_{29}NO_{10} \cdot HCl$ with a molecular weight of 564. It is a hygroscopic crystalline powder. The pH of a 5 mg/mL aqueous solution is 3 to 4. It is provided as a deep red sterile liquid in vials for intravenous administration only. Each mL contains 5.34 mg of daunorubicin hydrochloride, 9 mg sodium chloride; sodium hydroxide and/or hydrochloric acid (to adjust pH), and 99% of it is water for injection. The daunorubicin hydrochloride is administered intravenously in the treatment of acute lymphoblastic leukemia and acute myelogenous leukemia. Daunorubicin liposome preparation consists of the citrate salt and it is administered intravenously in the treatment of advanced Kaposi's sarcoma associated with acquired immunodeficiency syndrome (AIDS).

Doxorubicin Hydrochloride is the hydrochloride salt of doxorubicin, an anthracycline antibiotic with antineoplastic activity. Its molecular weight is 580 and its molecular formula is $C_{27}H_{29}NO_{11}$ HCl. It is soluble in water. The pH of the aqueous solutions of 5 mg/ml is 4.0-5.5. Doxorubicin Hydrochloride Injection, USP is a clear, red, sterile, isotonic aqueous solution provided in vials containing 10 mg/5 mL, 20 mg/10 mL, 50 mg/25 mL, 150 mg/75 mL, or 200 mg/100 mL of doxorubicin HCl. Each milliliter of solution contains 2 mg of doxorubicin HCl. Inactive ingredients include sodium chloride 0.9%, and 99% of the solution is water for injection. The pH of the solution is adjusted to 3.0 with hydrochloric acid. Doxorubicin HCl is indicated as a component of multi-agent adjuvant chemotherapy for treatment of women with axillary lymph node involvement following resection of primary breast cancer, acute lymphoblastic leukemia, acute myeloblastic leukemia, Hodgkin lymphoma, non-Hodgkin lymphoma, metastatic breast cancer, metastatic Wilms' tumor, Kaposi's sarcoma, metastatic neuroblastoma, metastatic soft tissue sarcoma, metastatic bone sarcoma, metastatic ovarian carcinoma, metastatic transitional cell bladder carcinoma, metastatic thyroid carcinoma, metastatic gastric carcinoma, metastatic bronchogenic carcinoma by intravenous injection.

Doxorubicin intercalates between base pairs in the DNA helix, thereby preventing DNA replication and ultimately inhibiting protein synthesis. The recommended dose of doxorubicin HCl for adjuvant breast cancer is 60 mg/m$^2$ administered as an intravenous bolus on day 1 of each 21-day treatment cycle, in combination with cyclophosphamide, for a total of four cycles. The analog of doxorubicin on the market is doxorubicin hydrochloride. The formulation may be doxorubicin hydrochloride injection liquid, liposome or doxorubicin hydrochloride injection powder.

Epirubicin is an epimer of doxorubicin and differs only from doxorubicin in the orientation of the C-4 hydroxyl group on the sugar. The available epirubicin product on the market is epirubicin hydrochloride, which is used in the treatment of gastric and breast cancer and is also indicated for the treatment of carcinoid, endometrial, lung, ovarian, esophageal and prostate cancers, as well as soft tissue sarcomas. Epirubicin hydrochloride is the hydrochloride salt of epirubicin, an anthracycline antibiotic with antineoplastic activity. Its molecular weight is 580 and its molecular formula is $C_{27}H_{30}ClNO_{11}$. It is soluble in water. The pH of the aqueous solutions of epirubicin hydrochloride 5 mg/ml is 4.0-5.5. Epirubicin hydrochloride is an anthracycline cytotoxic agent, intended for intravenous administration. Epirubicin hydrochloride is supplied as a sterile, clear, red solution and is available in polypropylene vials containing 50 and 200 mg of epirubicin hydrochloride as a preservative-free, ready-to-use solution. Each milliliter of solution contains 2 mg of epirubicin hydrochloride. Inactive ingredients include sodium chloride and water for injection.

Mitoxantrone, a DNA-reactive agent that intercalates into DNA through hydrogen bonding, causes crosslinks and strand breaks. Mitoxantrone also interferes with ribonucleic acid (RNA) and is a potent inhibitor of topoisomerase II, an enzyme responsible for uncoiling and repairing damaged DNA.

The molecular weight of mitoxantrone hydrochloride is 517.4 g/mol and its molecular formula is $C_{22}H_{30}Cl_2N_4O_6$. The product of mitoxantrone on the market is Mitoxantrone Hydrochloride Injection, which should be administered slowly into a freely flowing intravenous infusion. It must never be administered subcutaneously, intramuscularly, or intra-arterially. Mitoxantrone is used for advanced prostate cancer not responding to hormone treatment, acute myelogenous leukemia, breast cancer, Non-Hodgkin's lymphoma. Mitoxantrone Injection, USP (concentrate) is supplied as a concentrate that must be diluted prior to injection. The concentrate is a sterile, non-pyrogenic, dark blue aqueous solution containing mitoxantrone hydrochloride equivalent to 2 mg/ml mitoxantrone free base, with the following inactive ingredients: sodium chloride (0.800% w/v), sodium acetate (0.005% w/v), acetic acid (0.046% w/v), and water for injection. The solution has a pH of 3.0 to 4.5.

Amrubicin hydrochloride has the molecular formula of $C_{25}H_{26}ClNO_9$ and its molecular weight is 519.94. Amrubicin is a synthetic 9-amino-anthracycline with antineoplastic activity. Amrubicin intercalates into DNA and inhibits the activity of topoisomerase II, resulting in inhibition of DNA replication, and RNA and protein synthesis, followed by cell growth inhibition and cell death. This agent has demonstrated a higher level of anti-tumor activity than conventional anthracycline drugs without exhibiting any indication of the cumulative cardiac toxicity common to this class of compound. Amrubicin is not soluble in water, but soluble in DMSO. Its molecular weight is 483.5 g/mol and the molecular formula is $C_{25}H_{25}NO_9$.

Anthracyclines inhibit cancer through multiple pathways. For example, anthracyclines inhibit synthesis of DNA and some anthracyclines appear to inhibit the topoisomerase II enzyme. Anthracyclines are considered non-cell cycle specific drugs and are used on a wide range of cancers. Their major drawback is toxicity on heart muscle. Anthracycline hydrochloride is soluble in water, but anthracycline base is not soluble in water.

The side effects of anthracyclines, like other conventional chemotherapeutic agents, are linked to their cytotoxicity to non-malignant, proliferating normal cells and include nausea, vomiting, and alopecia. However, the major toxicities of anthracyclines, such as cardiotoxicity (e.g. cardiomyopathy and congestive heart failure) and myelosuppression, are major limitations on the use of these drugs. Anthracyclines such as doxorubicin also can cause severe local tissue necrosis. Anthracycline-induced-cardiotoxicity is irreversible and thus is an especially important consideration when considering use of these drugs in the treatment of malignancies in patients.

Strategies to limit the cardiotoxic effects of anthracyclines are being employed, including limiting the overall dosage, encapsulation into liposomes, combination treatment, use of cardio-protector medications, and synthesis of less harmful modified anthracyclines.

The extreme side effects of anticancer drugs are caused by the poor target specificity of such drugs, such that the drugs circulate through most normal organs of patients as well as intended target tumors. The poor target specificity causing side effects also results in decrease of the efficacy of chemotherapy because only a fraction of the drug is correctly targeted to target tumor cells. The efficacy of chemotherapy is further decreased by poor retention of the anticancer drugs within the target tumors.

Vinca alkaloid antineoplastic drugs are alkaloids extracted from *Catharanthus roseus* of apocynaceae alkaloids that are medically available and have been used in clinics, include vinblastine, vincristine, vindesine, vinflunine and vinorelbine. Binding of the vinca alkaloids to the binding site of tubulin interrupts microtubule segregation. Studies have shown that the cytotoxicity of vinca alkaloid antineoplastic drugs is achieved by binding with tubuline, thus stopping the mitosis and proliferation of cancer cells. In addition to nuclear collapse and vacuolar vacuolization, vinca alkaloid antineoplastic drugs can also act on the cell membrane, interfere with the transport of amino acids by the cell membrane, inhibit protein synthesis and RNA synthesis by inhibiting the activity of the RNA synthesis enzyme, and can kill cancer cells in many ways.

Vinca alkaloid antineoplastic drugs that are medically available are vinca alkaloid sulfate injections which are aqueous injections, such as vinblastine sulfate injection, vincristine sulfate injection, vindesine sulfate injection, etc. Vinblastine sulfate injection, vincristine sulfate injection and vindesine sulfate injection are all water soluble and their side effects include blood problems, nervous system problems and loss of hair.

Vinblastine sulphate is amorphous powder or crystalline powder which is white to light yellow. It is very slightly soluble in ethanol and practically insoluble in ether. One part is soluble in 10 parts of water. The molecular formula of vinblastine sulphate is $C_{46}H_{58}N_4O_9 \cdot H_2SO_4$ and the molecular weight is 909.05.

Vinblastine sulfate is indicated in the palliative treatment of e.g. the following diseases: Hodgkin's disease, lymphocytic lymphoma, histiocytic lymphoma, mycosis fungoides, advanced carcinoma of the testis, Kaposi's sarcoma, Letterer-Siwe disease (histiocytosis X), carcinoma of the breast unresponsive to appropriate endocrine hormonal and surgery therapy, and choriocarcinoma resistant to other chemotherapeutic agents. The major adverse effect of vinblastine is hematologic toxicity.

Vinblastine has some immunosuppressant effect. The major route of excretion may be through the biliary system. Following IV administration, the drug is rapidly cleared from the blood and distributed into body tissues. Vinblastine sulfate crosses the blood brain barrier poorly and does not appear in the CSF in therapeutic concentrations. Vinblastine is reported to be extensively metabolized, primarily in the liver to de-acetylvinblastine, which is more active than the parent compound on a weight basis. Pharmacokinetic studies in patients with cancer have shown a triphasic serum decay pattern following rapid intravenous injection. The initial, middle, and terminal half-lives are 3.7 minutes, 1.6 hours, and 24.8 hours, respectively. The antitumor activity of vinblastine is thought to be due primarily to inhibition of mitosis at metaphase through its interaction with tubulin. Vinblastine binds to the micro tubular proteins of the mitotic spindle, leading to crystallization of the microtubule and mitotic arrest or cell death. In high concentrations, vinblastine also exerts complex effects on nucleic acid and protein synthesis. Vinblastine reportedly also interferes with amino acid metabolism by blocking cellular utilization of glutamic acid and thus inhibits purine synthesis, the citric acid cycle, and the formation of urea. The vinblastine sulfate product currently available on the market is only for IV injection and there is no vinblastine base injection product on the market, nor is there an intratumor injection product on the market.

Vincristine binds irreversibly to microtubules and spindle proteins in S phase of the cell cycle and interferes with the formation of the mitotic spindle, thereby arresting the division of tumor cells in metaphase. This agent also depolymerizes microtubules and may also interfere with amino acid, c-AMP, glutathione metabolism, cellular respiration, nucleic acid and lipid biosynthesis. It is used commonly as the corresponding sulfate salt, as an intravenous chemotherapy drug for the treatment of leukemia, lymphoma, myeloma, breast cancer, head and neck cancer.

The molecular formula of vincristine is $C_{46}H_{56}N_4O_{10}$ and its molecular weight is 825. It is a powder at room temperature and its $LD_{50}$ i.p. in mice is 5.2 mg/kg. Vincristine is practically insoluble in water and the solubility in water is 2.27 mg/L at 25° C. It is soluble in alcohol, acetone, and chloroform.

Vincristine sulfate is a white to slight yellow amorphous or crystalline powder and is freely soluble in water. It is practically insoluble in ether and is slightly soluble in alcohol. The molecular formula of vincristine sulfate is $C_{46}H_{56}N_4O_{10} \cdot H_2SO_4$ and its molecular weight is 923.

The product of vincristine sulfate on the market is for IV injection. Vincristine sulfate injection is indicated in acute leukemia. Vincristine sulfate injection has also been shown to be useful in combination with other oncolytic agents in Hodgkin's disease, non-Hodgkin's malignant lymphomas, rhabdomyosarcoma, neuroblastoma, and Wilms' tumor. Vincristine is used as a component of various chemotherapeutic regimens for the palliative treatment of neuroblastoma. Vincristine sulfate injections contain more than 95% of water by volume.

Vindesine sulfate is the sulfate salt of vindesine. Vindesine binds to and stabilizes tubulin, thereby interrupting tubulin polymerization and preventing the formation of the mitotic spindle and cell division; treated cells are unable to undergo mitosis and are arrested in metaphase. Its molecular weight is 852 g/mol. Its molecular formula is $C_{43}H_{55}N_5O_7 \cdot H_2SO_4$. Acute shortness of breath and severe bronchospasm have frequently been reported with combination therapy including vinca alkaloids; the reaction may occur within minutes or several hours after the vinca alkaloid is injected. Neurologic toxicity may occur early in treatment and may be more severe if used concomitantly with other drugs having a neurotoxic potential.

The product of vindesine sulfate on the market is for IV injection. Vindesine sulfate injections is an aqueous solution and is indicated for the treatment of acute lymphocytic leukemia of childhood that is resistant to vincristine and non-oat cell lung cancer. Vindesine causes the arrest of cells in metaphase mitosis.

Alkylating agents are compounds that work by adding an alkyl group to the guanine base of the DNA molecule, preventing the strands of the double helix from linking, which in turn causes breakage of the DNA strands, affecting the ability of the cancer cell to multiply. Eventually, the cancer cell dies. The special alkylating agents of known nitrogen mustards include bendamustine, chlorambucil, ifosfamide, cyclophosphamide, mechlorethamine, melphalan. All of these nitrogen mustards can be made into an intratumor injection.

Mechlorethamine is nitrogen mustard. The molecular formula is $C_5H_{11}C_{12}N$ and the molecular weight is 156 g/mol. Mechlorethamine is a synthetic agent related to sulphur mustard with antineoplastic and immunosuppressive property. It is a colorless to yellow liquid. It is very slightly soluble in water; miscible with dimethyl formamide, carbon disulfide, carbon tetrachloride and many organic solvents and oils. Nitrogen mustards form salts with hydrochloric acid, which are freely soluble in water and their toxic action is equivalent to the initial nitrogen mustard.

Mechlorethamine hydrochloride injection is an antineoplastic agent for intravenous use that has been in clinical use for more than 60 years, given systemically in combination with other antineoplastic agents to treat Hodgkin disease, chronic leukemias, lung cancer and polycythemia vera. Currently, however, it is used largely as a topical gel for therapy of cutaneous T-cell lymphomas and mycosis fungoides, also for the palliative treatment of metastatic carcinoma resulting in effusion.

Bendamustine Hydrochloride has a molecular formula of $C_{16}H_{22}Cl_3N_3O_2$ and its molecular weight is 394.7 g/mol. Bendamustine hydrochloride is soluble in water. Bendamustine HCL injection is for intravenous administration in the treatment of chronic lymphocytic leukemia and refractory forms of non-Hodgkin lymphoma. Bendamustine intravenous therapy is associated with minor transient serum enzyme elevations during treatment and rare instances of clinically apparent liver injury. Bendamustine also has potent immunosuppressive activity and can cause reactivation of chronic hepatitis B that can be severe and even fatal. The side effects of water-soluble anticancer drugs are caused by the poor target specificity of such drugs, such that the drugs circulate through most normal organs of patients as well as intended target tumors. The poor target specificity also results in decrease of the efficacy of chemotherapy because only a fraction of the drug is correctly targeted to target tumor cells. The efficacy of chemotherapy is further decreased by poor retention of the acidic anti-cancer drugs within the target tumors.

There are many injectable chemotherapeutic formulations approved for marketing in the U.S., e.g., doxorubicin hydrochloride injection, doxorubicin hydrochloride liposome injection, daunorubicin hydrochloride injection, epirubicin hydrochloride injection, amrubicin hydrochloride, mitoxantrone hydrochloride injection, eribulin mesylate cisplatin, oxaliplatin, fluorouracil injection and daunorubicin liposome injection.

It is a goal of the present invention to provide a delivery system and method capable of administering chemotherapy, and in particular anthracyclines, directly to a malignant mass in a mammal (e.g., human), providing a maximum killing effect without the severe side effects.

OBJECTS AND SUMMARY OF THE INVENTION

It is an object of the present invention to provide formulations and methods for treating a malignant mass in an animal.

It is another object of the present invention to provide methods of manufacturing a basic chemotherapeutic intratumor injection.

It is another object of the present invention to provide a method for administering anthracycline base to animals (e.g., humans) which reduces the untoward side effects currently experienced with the administration of intravenous injection.

It is another object of the present invention to provide a method for administering anthracycline base to animals (e.g., humans), which increase the cure rate of chemotherapy.

It is another object of the present invention to provide a method for administering a vinca alkaloid base to an animal (e.g., human) which reduces the untoward side effects currently experienced with the administration of an intravenous injection and raises the cure rate of the anticancer therapy.

It is another object of the present invention to provide a method for administering a basic alkylating agent to an animal (e.g., human), which reduces the untoward side effects currently experienced with the administration of an intravenous injection and raises the cure rate of the anticancer therapy.

It is another object of the present invention to provide stable formulations of basic anthracyclines, of basic eribulin, of basic vinca alkaloids, or of basic alkylating agents which are useful in the methods of the present invention.

It is another object of the invention to produce a chemotherapeutic base injection having a high concentration of basic chemotherapeutic drug, an evenly distributed solution, a solution free of bacteria and having a simple method of production.

In accordance with the above objects and others, the present invention is directed to a method of treating a malignant mass in a mammal, comprising administering an injectable formulation comprising a drug consisting of a therapeutically effective amount of a basic chemotherapeutic drugs, wherein the drug is dissolved, suspended or dispersed in a biocompatible carrier directly into the malignant mass. In certain preferred embodiments, the formulation comprises a stable form of a basic anthracycline, a basic vinca alkaloid, a basic eribulin or a basic alkylating agent.

The present invention is also directed to an injectable pharmaceutical formulation comprising a drug consisting of an anthracycline(s) base (e.g. daunorubicin base, doxorubicin base, epirubicin base, amrubicin base or mitoxantrone base), wherein the drug is dissolved or suspended in a pharmaceutically acceptable carrier for administration directly into a malignant mass in a mammal (e.g., human). In certain preferred embodiments, the injectable pharmaceutical formulation is stable. In certain embodiments, the formulation is a solution, a suspension or a water in oil emulsion. In certain embodiments, the anthracycline base is in a water in emulsion which comprises a small amount of an aqueous solution of sodium chloride and acetic acid dispersed in an oleic acid and ethanol mixture as microspheres, wherein the acetic acid acts as a buffer to increase the solubility of the basic anthracycline in the organic solvent. In certain preferred embodiments, the basic anthracycline is a water in oil nano emulsion of the injectable pharmaceutical formulation and is stable. In preferred embodiments of the formulation (e.g. daunorubicin formulation), the amount of water in the nano emulsion is more than 4% but less than 15% of the volume of the emulsion injection.

The present invention is also directed to an injectable pharmaceutical formulation comprising a drug consisting of a vinca alkaloid base (e.g. vinblastine base, vincristine base or vindesine base), wherein the drug is dissolved or suspended in a pharmaceutically acceptable carrier for administration directly into a malignant mass in a mammal (e.g., human). In certain preferred embodiments, the injectable pharmaceutical formulation is stable. In certain embodiments, the formulation is a solution, a suspension or a water in oil emulsion. In certain embodiments, the vinca alkaloid base is in a water in oil emulsion which comprises a small amount of an aqueous solution of sodium sulfate and acetic acid dispersed in a mixture of ethanol and an oleic acid, glycerol or median chain triglyceride as microspheres, wherein the acetic acid acts as the buffer to increase the solubility of the base in the organic solvent. In certain preferred embodiments, the basic vinca alkaloid base is a water in oil nano emulsion of the injectable pharmaceutical formulation and is stable. In certain preferred embodiments, the amount of water in the water in oil emulsion of vinca alkaloid base is from about 1 to about 10% of the volume of the emulsion.

The present invention is also directed to an injectable pharmaceutical formulation of a drug comprising an alkylating basic drug dissolved or suspended in a pharmaceutically acceptable carrier for administration directly into a malignant mass in a mammal (e.g., human). In certain preferred embodiments, the injectable pharmaceutical formulation is stable. In certain preferred embodiments, the alkylating basic drug is a mechlorethamine base. In certain preferred embodiments, the alkylating basic drug is a bendamustine base. Such formulation may be a solution, suspension or water in oil emulsion. In certain embodiments, the alkylating basic drug is in a water in oil emulsion which comprises a small amount of an aqueous solution of sodium chloride and acetic acid dispersed in a mixture of ethanol and an oleic acid, glycerol or median chain triglyceride as microspheres, wherein the acetic acid acts as a buffer to increase the solubility of the base in the organic solvent. In certain preferred embodiments, the water in oil nano emulsion of the injectable pharmaceutical formulation is stable. In certain preferred embodiments, the amount of water in the water in oil emulsion of the basic alkylating drug is from about 1% to about 10% of the volume of the emulsion.

The present invention is also directed to an intratumor injectable formulation comprising a basic chemotherapeutic drug selected from the group consisting of an anthracycline base, a vinca alkaloid base, eribulin base, and an alkylating agent base and a pharmaceutically acceptable biocompatible carrier for injection of the drug selected from the group consisting of PEG, an oleic acid, an alcohol, a glycerin, a median chain triglyceride, a vegetable oil, and mixtures thereof, wherein the intratumor injectable formulation is a solution, suspension or water in oil emulsion. In certain embodiments, the basic chemotherapeutic drug of the intratumor injectable formulation of the present invention can be a vinca alkaloid base selected from the group consisting of vinblastine, vincristine, vindesine and mixtures thereof, an anthracycline base selected from the group consisting of doxorubicin, epirubicin, daunorubicin, mitoxantrone, idarubicin, amrubicin, aclarubicin and valrubicin and mixtures thereof; or an alkylating agent base selected from the group consisting of bendamustine, mechlorethamine, procarbazine, and mixtures thereof. In certain preferred embodiments, the basic chemotherapeutic drug is doxorubicin base and the biocompatible carrier for injection is a mixture of oleic acid and an alcohol selected from the group consisting of ethanol, propylene glycol, benzyl alcohol, tert-butyl alcohol 9- and combinations thereof. In other embodiments, the pharmaceutically acceptable biocompatible carrier for injection comprises an alcohol selected from the group consisting of ethanol, benzyl alcohol and combinations thereof.

In embodiments of the present invention, the intratumor injectable formulation comprises a pharmaceutically acceptable biocompatible carrier for injection which is an organic liquid selected from the group consisting of a PEG of molecular weight of 200 to 400, a median chain triglyceride, oleic acid, glycerol, a liquid alcohol comprising ethanol and benzyl alcohol, and mixtures thereof such that the formulation is a solution or suspension. In certain embodiments, the basic chemotherapeutic drug is selected from the group consisting of vinblastine base, vincristine base and vindesine base, and the pharmaceutically acceptable biocompatible carrier for injection is selected from the group consisting of an organic liquid mixture comprising a median chain triglyceride, oleic acid, glycerol, acetic acid and an alcohol selected from the group consisting of ethanol, benzyl alcohol, and combinations thereof, such that the formulation is a solution or suspension. In certain embodiments, the basic chemotherapeutic drug is selected from vinblastine base, vincristine base or vindesine base, and the pharmaceutically acceptable biocompatible carrier is a mixture of an ethanol, an organic liquid selected from the group consisting a median chain triglyceride, glycerol or oleic acid, and an organic acid, such that the formulation is a solution or suspension. In certain preferred embodiments, the organic acid is acetic acid. In other embodiments, the basic chemotherapeutic drug comprises bendamustine base and the pharmaceutically acceptable biocompatible carrier is a mixture selected from the group consisting of ethanol mixed with a PEG of molecular weight from about 200 to 400 and oleic acid mixed with acetic acid, such that the formulation is a solution or suspension.

In certain embodiments of the present invention, the basic chemotherapeutic drug is a desalinated salt form of a chemotherapeutic drug, wherein the biocompatible carrier is selected from the group consisting of a PEG of molecular weight of 200 to 400, a median chain triglyceride, oleic acid, glycerol, a liquid alcohol comprising ethanol and benzyl alcohol, and combinations thereof, wherein the formulation comprises water in an amount of less than 10% of the total volume of the injectable formulation and a salt selected from the group consisting of sodium sulfate, sodium chloride, potassium sulfate, potassium chloride, sodium mesylate, potassium mesylate and mixtures thereof, such that the formulation is an emulsion. In certain other embodiments of the present invention, the basic chemotherapeutic drug is a desalinated salt form of a chemotherapeutic drug, wherein the biocompatible carrier is selected from the group consisting of a PEG of molecular weight of 200 to 400, a median chain triglyceride, oleic acid, glycerol, a liquid alcohol comprising ethanol and benzyl alcohol, and combinations thereof, wherein the formulation comprises water in an amount of less than 15% of the total volume of the injectable formulation and a salt selected from the group consisting of sulfate, chloride, mesylate and mixtures thereof, such that the formulation is an water in oil emulsion. In certain embodiments, the injectable formulation is an emulsion comprising the basic chemotherapeutic agent, the biocompatible carrier, an alcohol comprised of ethanol or benzyl alcohol, a buffer comprised of an organic acid and wherein the organic acid is selected from the group consisting of acetic acid, malic acid, fumaric acid, tartaric acid, succinic acid, maleic acid, citric acid, ascorbic acid, and mixtures thereof, and wherein the water is less than 15% of the injectable formulation. In other embodiments, the injectable formulation is an emulsion comprising the basic chemotherapeutic agent, the biocompatible carrier, an alcohol comprised of ethanol or benzyl alcohol, sodium or potassium chloride, a buffer comprised of an organic acid and wherein the organic acid is selected from the group consisting of acetic acid, malic acid, fumaric acid, tartaric acid, succinic acid, maleic acid, citric acid, ascorbic acid, and mixtures thereof, and wherein the water is less than 15% of the injectable formulation and the amount of organic solvent is more than 85% of the volume of the emulsion. In certain other embodiments, the injectable formulation is a water in oil emulsion comprising an anthracycline base selected from the group consisting of doxorubicin base, epirubicin base, daunorubicin base, amrubicin base and mitoxantrone base, an oleic acid, acetic acid, less than 15% of water by volume of the emulsion and an alcohol, wherein the alcohol is selected from the group consisting of ethanol, benzyl alcohol or combinations thereof. In certain embodiments, the formulation is a water in oil emulsion comprising the basic chemotherapeutic agent, oleic acid, an alcohol, acetic acid, sodium chloride and from about 4% to about 15% of water by volume of the emulsion, wherein the basic chemotherapeutic agent selected from the group consisting of daunorubicin base, epirubicin base, amrubicin base, doxorubicin base, mitoxantrone base. In certain preferred embodiments, the formulation is a water in oil emulsion comprising the basic chemotherapeutic agent, oleic acid, an alcohol, acetic acid, sulfate or chloride, and from about 4% to about 15% of water by volume of the emulsion, wherein the basic chemotherapeutic agent selected from the group consisting of daunorubicin base, epirubicin base, doxorubicin base, mitoxantrone base and amrubicin base. In certain preferred embodiments, the alcohol is selected from the group consisting of ethanol, benzyl alcohol, and combinations thereof. In certain embodiments, the basic chemotherapeutic drug is selected from the group consisting of desalinated vinblastine sulfate, vincristine sulfate and vindesine sulfate, wherein the biocompatible carrier is selected from the group consisting of a median chain triglyceride, oleic acid, glycerol and combinations thereof and the formulation further comprises acetic acid, sodium sulfate and a small amount of water, such that the formulation is an emulsion containing less than about 10% of water by volume of the emulsion. In other embodiments, the basic chemotherapeutic drug is selected from the group consisting of a vincristine base, a vinblastine base and a vindesine base wherein the biocompatible carrier is a mixture of an alcohol comprising ethanol or benzyl alcohol and a median chain triglyceride, glycerol or oleic acid, and wherein the formulation further comprises acetic acid, sodium sulfate and a small amount of water, such that the formulation is a water in oil emulsion containing from about 1% to about 10% of water by volume of the emulsion. In certain preferred embodiments, the basic chemotherapeutic drug is selected from the group consisting of a vincristine base, a vinblastine base and a vindesine base wherein the biocompatible carrier is a mixture of an alcohol comprising ethanol or benzyl alcohol and a median chain triglyceride, glycerol or oleic acid, and wherein the formulation further comprises acetic acid, sulfate or chloride salt and a small amount of water, such that the formulation is a water in oil emulsion containing from about 0.5% to about 5% of water by volume of the emulsion.

In certain embodiments, the basic chemotherapeutic drug comprises bendamustine base dissolved or suspended in a mixture selected from the group consisting of ethanol mixed with a PEG of molecular weight from about 200 to 400, glycerol or oleic acid mixed with acetic acid. In certain preferred embodiments, the basic chemotherapeutic drug comprises bendamustine base and the pharmaceutically acceptable biocompatible carrier is a mixture selected from the group consisting of ethanol mixed with a PEG of molecular weight from about 200 to 400 or oleic acid mixed with acetic acid, such that the formulation is a solution or suspension. In other embodiments, the basic chemotherapeutic drug comprises bendamustine base and the pharmaceutically acceptable biocompatible carrier is a mixture selected from the group consisting of oleic acid, glycerol and PEG of molecular weight of 200 to 400 and an ethanol, and the formulation further comprises a water phase of acetic acid, sodium chloride and a small amount of water, such that the formulation is an emulsion having from about 2% to about 10% of water by volume of the emulsion. In certain preferred embodiments, the basic chemotherapeutic drug formulation is a water in oil emulsion comprises bendamustine base and wherein the pharmaceutically acceptable biocompatible carrier is a mixture of oleic acid and an ethanol, the formulation further comprises a water phase of acetic acid, sodium or potassium chloride and from about 2% to about 10% of water by volume of the emulsion. In certain preferred embodiments, the basic chemotherapeutic drug formulation is a water in oil emulsion comprises bendamustine base and wherein the pharmaceutically acceptable biocompatible carrier is a mixture of glycerol and an ethanol, the formulation further comprising a water phase of acetic acid, sodium or potassium chloride and a small amount of water from about 2% to about 10% of water by volume of the emulsion. In certain preferred embodiments, the formulation is a water in oil emulsion comprising bendamustine base dissolved in a mixture of a PEG of molecular weight of 200 to 400 and an ethanol and wherein the emulsion further comprises a water phase of acetic acid, sodium or potassium chloride and from about 2% to about 10% of water by volume of the emulsion.

In other embodiments, the basic chemotherapeutic drug comprises mechlorethamine base and the pharmaceutically acceptable biocompatible carrier is a mixture of ethanol with a median chain triglyceride or glycerol, and the formulation further comprises acetic acid, such that the formulation is a solution or a suspension. In other embodiments, basic chemotherapeutic drug is mechlorethamine base and wherein the pharmaceutically acceptable biocompatible carrier is a mixture of glycerol and ethanol, the formulation further comprising acetic acid, sodium chloride or potassium chloride and less than about 10% of water by volume of the formulation, such that the formulation is an emulsion. In certain other embodiments, the basic chemotherapeutic drug is mechlorethamine base and the pharmaceutically acceptable biocompatible carrier is a mixture of median chain triglyceride and ethanol, and the formulation further comprising acetic acid, sodium chloride or potassium chloride and less than about 5% of water by volume of the formulation, such that the formulation is an emulsion. In certain preferred embodiments, the basic chemotherapeutic drug is mechlorethamine base and wherein the pharmaceutically acceptable biocompatible carrier is a mixture of a median chain triglyceride and ethanol, the formulation further comprising acetic acid, and less than about 1% of water by volume of the formulation. In certain other preferred embodiments, the basic chemotherapeutic drug comprises mechlorethamine base and the pharmaceutically acceptable biocompatible carrier is a mixture of ethanol with a median chain triglyceride, the formulation further comprising acetic acid, sodium or potassium chloride and less than about 10% of water by volume of the formulation, such that the formulation is an emulsion.

The present invention is also directed to an injectable pharmaceutical formulation of a drug comprising an anthracycline(s) base dissolved or suspended in a pharmaceutically acceptable carrier for administration directly into a malignant mass in a mammal (e.g., human). In certain preferred embodiments, the anthracycline base is doxorubicin base. In certain preferred embodiments, the anthracycline base is daunorubicin base. In other preferred embodiments, the anthracycline base is epirubicin base. In other preferred embodiments, the anthracycline base comprises mitoxantrone base. In other preferred embodiments, the anthracycline base comprises amrubicin base. In certain preferred embodiments, the anthracycline base comprises aclarubicin base. In other preferred embodiments the anthracycline base comprises idarubicin base, pirarubicin base or valrubicin base. In certain embodiments, the intratumor injectable formulation is a solution or suspension, wherein the basic chemotherapeutic drug is dissolved in the pharmaceutically acceptable biocompatible carrier for injection and wherein the pharmaceutically acceptable biocompatible carrier for injection is an organic liquid selected from the group consisting of a PEG of molecular weight of 200 to 400, a median chain triglyceride, oleic acid, glycerol, a liquid alcohol comprising ethanol and benzyl alcohol, and mixtures thereof.

The present invention is also directed to an injectable pharmaceutical formulation of a drug comprising a vinca alkaloid base dissolved or suspended in a pharmaceutically acceptable carrier for administration directly into a malignant mass in a mammal (e.g., human). In certain preferred embodiments, the vinca alkaloid base is vinblastine base. In certain preferred embodiments, the vinca alkaloid base is vincristine base. In other preferred embodiments, the vinca alkaloid base is vindesine base.

In certain embodiments, the basic chemotherapeutic drug comprises eribulin base dissolved or suspended in a mixture selected from the group consisting of ethanol mixed with a PEG of molecular weight from about 200 to 400, glycerol, a median chain triglyceride or oleic acid mixed with acetic acid. In other embodiments, the basic chemotherapeutic drug comprises eribulin base and the pharmaceutically acceptable biocompatible carrier is a mixture selected from the group consisting of oleic acid, glycerol and a PEG of molecular weight of 200 to 400, a median chain triglyceride and an ethanol, and the formulation further comprises a water phase of acetic acid, sodium mesylate and a small amount of water, such that the formulation is an emulsion having from about 1% to about 5% of water by volume of the emulsion. In certain preferred embodiments, wherein the basic chemotherapeutic drug is eribulin base, wherein the biocompatible carrier is a mixture of an alcohol comprising ethanol or benzyl alcohol and a median chain triglyceride, glycerol, PEG of molecular weight 200 to 400 or oleic acid, and wherein the formulation further comprises acetic acid, sodium mesylate or potassium mesylate and a small amount of water from about 0.5% to about 5% of water by volume of the formulation which is an emulsion.

In certain embodiments of the present invention, the pharmaceutically acceptable carrier is a liquid comprising a PEG, an oleic acid, glycerol, a median chain triglyceride, vegetable oil, surfactant, an alcohol or combinations thereof. In certain preferred embodiments, the PEG has a molecular weight of from about $PEG_{200}$ to about $PEG_{400}$. In certain preferred embodiments, the alcohol is ethanol, propylene, benzyl alcohol, tert-butyl alcohol or mixtures thereof. In certain preferred embodiments, the pharmaceutically acceptable carrier includes ethanol. In certain other preferred embodiments, the pharmaceutically acceptable carrier includes benzyl alcohol.

In certain embodiments, the malignant mass may be in a location in the mammal selected from the group consisting of brain, head, eye, mouth, tongue, neck, thyroid, gastrointestinal system, liver, pancreas, gall bladder, lung, respiratory system, urogenital system, breast, lymphatic system, cardiovascular system, nervous system, skin, thorax, pleural membrane, mesothelioma, muscular skeletal system, abdomen with primary or secondary nature. The malignant mass may be one that has metastasized from another organ in the mammal. In certain preferred embodiments, the biocompatible carrier comprises a polyethylene glycol (PEG), an oleic acid, glycerol, a median chain triglyceride, vegetable oil, surfactant, an ethanol, propylene glycol, benzyl alcohol, tert-butyl alcohol or any combination of the above.

In certain preferred embodiments, the injectable formulation is administered through a syringe or a needle of a fiberscope.

In certain embodiments, the malignant mass is:
(i) a superficial malignant disease of skin, eye, tongue, mouth, thyroid, breast, cervix, uterus, anus, prostate, vagina, sarcoma of the bone, carcinoma of urethra, etc. and the basic chemotherapeutic drug injection (e.g. an anthracycline base, a vinca alkaloid base or an alkylating base) can be injected using a syringe directly into the malignant mass, or
(ii) a cancer of the nasopharynx and the basic chemotherapeutic drug injection can be injected into the malignant mass with the syringe or needle through a nasopharyngoscope; or
(iii) a cancer of the liver, kidney, pancreas and gall bladder and the basic chemotherapeutic drug injection can be injected using a syringe through the skin into the malignant mass with the assistance of ultrasound, or via a hole in the abdominal wall made during laparoscopic surgery into the malignant mass; or
(iv) a cancer of the ovary, oviduct, metastasis of lymph node or direct peritoneum invasion of the abdominal cavity and the basic chemotherapeutic drug injection can be injected with the needle into the malignant mass through the holes of a laparoscopic surgery; or
(v) a carcinoma or sarcoma of esophagus, stomach, duodenum, small intestine and the basic chemotherapeutic drug injection can be injected with the needle into the malignant mass through an enteroscope or through the holes made during laparoscopic surgery or holes made during thoracoscopic surgery; or
(vi) a carcinoma or sarcoma of the large intestine and rectum and the basic chemotherapeutic drug injection can be injected with the needle into the malignant mass through colonoscopy or through the holes of abdominal wall of laparoscopic surgery; or
(vii) a carcinoma or sarcoma of the throat, lung and trachea and the basic chemotherapeutic drug injection can be injected with the needle of a fiber bronchoscope into the malignant mass; or
(viii) a carcinoma of the lung, trachea or of the organ in the thorax, and the basicchemotherapeutic drug injection can be injected with a syringe with the assistance of ultrasound, x-ray, CT scan, MR scan or via the holes of thoracoscopic surgery; or
(ix) a carcinoma or sarcoma of the urinary bladder and the basic chemotherapeutic drug injection can be injected into the malignant mass with a needle through a cystoscope, or through the holes in the abdominal wall made during laparoscopic surgery;
(x) a carcinoma or sarcoma of the uterus and the basic chemotherapeutic drug injection can be injected into the malignant mass with a syringe of a hysteroscope; or through the holes in the abdominal wall made during laparoscopic surgery;
(xi) a carcinoma or sarcoma of pharynx and larynx and the basic chemotherapeutic drug injection can be injected into the malignant mass with a needle through the laryngoscope; or
(xii) a carcinoma of the brain and the basic chemotherapeutic drug injection can be injected with a needle into the malignant mass after a hole is drilled in the corresponding bone of the skull with the help of X-ray, CT scan or MR scan; or
(xiii) a carcinoma of the testicle(s), the epididymis, penis, and/or vagina and the basic chemotherapeutic drug injection can be injected with a needle into the malignant mass directly without dilution.

The invention is further directed, in part, to an injectable formulation comprising a drug consisting of a therapeutically effective amount of a basic chemotherapeutic drug injection (e.g. an anthracycline base, eribulin base, a vinca alkaloid base or an alkylating base) and a pharmaceutically acceptable carrier for injection comprising a PEG having a molecular weight of from about $PEG_{200}$ to about $PEG_{400}$, an alcohol, glycerol, a median chain triglyceride, vegetable oil, an oleic acid or a mixture of thereof. In certain preferred embodiments, the alcohol is ethanol, propylene glycol, benzyl alcohol, tert-butyl alcohol or any combination of the above. In certain preferred embodiments, the alcohol is ethanol, benzyl alcohol or combinations thereof.

In certain preferred embodiments, the anthracycline base is doxorubicin base, daunorubicin base, epirubicin base, amrubicin base, pirarubicin base, valrubicin base, aclarubicin base, idarubicin base and mitoxantrone base.

In certain preferred embodiments, the vinca alkaloid base is vinblastine base, vincristine base and or vindesine base.

In certain preferred embodiments, the alkylating agent base is mechlorethamine base or bendamustine base.

In certain preferred embodiments, the anthracycline base is epirubicin base and the biocompatible carrier for injection is a PEG having a molecular weight from about $PEG_{200}$ to about $PEG_{400}$ In certain preferred embodiments, the anthracycline base is epirubicin base and the biocompatible carrier for injection is an oleic acid.

In certain preferred embodiments, the anthracycline base injection is a solution or a suspension comprising epirubicin base, ethanol, oleic acid and acetic acid.

In certain preferred embodiments, the anthracycline base injection is a water in oil emulsion comprising epirubicin base, sodium chloride, ethanol, oleic acid, acetic acid and from about 3 to about 15% of water.

In certain preferred embodiments, the anthracycline base is daunorubicin base and the biocompatible carrier for injection is an oleic acid.

In certain preferred embodiments, the anthracycline base is daunorubicin base and the biocompatible carrier for injection is a mixture of oleic acid, ethanol and acetic acid.

In certain preferred embodiments, the anthracycline base is epirubicin base and the biocompatible carrier for injection is a mixture of ethanol and a PEG having a molecular weight of from about $PEG_{200}$ to about $PEG_{400}$. In certain preferred embodiments, the anthracycline base is daunorubicin base and the biocompatible carrier for injection is ethanol.

In certain preferred embodiments, the anthracycline base is daunorubicin base and the biocompatible carrier for injection is PEG of molecular weight from about $PEG_{200}$ to about $PEG_{400}$.

In certain preferred embodiments, the anthracycline base is daunorubicin base and the biocompatible carrier for injection is a mixture of oleic acid and ethanol.

In certain preferred embodiments, the anthracycline base is daunorubicin base and the biocompatible carrier for injection is a mixture of a PEG having a molecular weight from about $PEG_{200}$ to about $PEG_{400}$ and ethanol.

In certain preferred embodiments, the anthracycline base injection is a solution or suspension comprising daunorubicin base and the biocompatible carrier for injection is a mixture of an ethanol, oleic acid and acetic acid.

In certain preferred embodiments, the anthracycline base is mitoxantrone base and the biocompatible carrier for injection is aqueous ethanol.

In certain preferred embodiments, the anthracycline base injection is a water in oil emulsion comprising daunorubicin base, sodium chloride and ethanol, oleic acid, acetic acid and from about 3% to about 10% of water. In other embodiments, the anthracycline base injection is a water in oil emulsion comprising daunorubicin base, sodium chloride and ethanol, oleic acid, acetic acid and from about 1% to about 10% of water. In other embodiments, the anthracycline base injection is a water in oil emulsion comprising daunorubicin base, sodium chloride and ethanol, oleic acid, acetic acid and from about 4% to about 10% of water. In other preferred embodiments, the formulation is a water in oil emulsion comprising daunorubicin base, oleic acid, ethanol, acetic acid, sodium or potassium chloride and from about 4% to about 10% of water by volume of the emulsion.

In certain preferred embodiments, the formulation is a water in oil emulsion comprising amrubicin base, oleic acid, ethanol, acetic acid, sodium or potassium chloride and from about 4% to about 10% of water by volume of the emulsion.

In certain preferred embodiments, the formulation is a water in oil emulsion comprising mitoxantrone base, oleic acid, glycerol, ethanol, acetic acid, sodium or potassium chloride and from about 2% to about 10% of water by volume of the emulsion.

In certain preferred embodiments, the anthracycline base is mitoxantrone base and the biocompatible carrier for injection is a mixture of a PEG having a molecular weight from about $PEG_{200}$ to about $PEG_{400}$ with ethanol.

In certain preferred embodiments, the anthracycline base is mitoxantrone base and the biocompatible carrier for injection is a mixture of a PEG having a molecular weight from about $PEG_{200}$ to about $PEG_{400}$ and an organic acid comprising maleic acid, succinic acid, malic acid, tartaric acid, citric acid, fumaric acid, tartaric acid, and combinations thereof.

In certain preferred embodiments, the anthracycline base is mitoxantrone base and the biocompatible carrier for injection is a mixture of oleic acid with ethanol.

In certain preferred embodiments, the anthracycline base is mitoxantrone base and the biocompatible carrier for injection is a mixture of oleic acid and an organic acid.

In certain preferred embodiments, the anthracycline base is mitoxantrone base and the biocompatible carrier for injection is a mixture of oleic acid, ethanol and acetic acid.

In certain preferred embodiments, the anthracycline base injection is a solution or suspension comprising mitoxantrone base, ethanol, oleic acid and acetic acid.

In certain preferred embodiments, the anthracycline base injection is a solution or suspension comprising mitoxantrone base, ethanol, glycerol and acetic acid.

In certain preferred embodiments, the formulation is a solution or a suspension comprising mitoxantrone base, ethanol and acetic acid and further including either oleic acid or glycerol.

In certain preferred embodiments, the anthracycline base injection is a water in oil emulsion comprising mitoxantrone base, sodium chloride, ethanol, oleic acid, acetic acid and from about 3% to about 10% of water.

In certain preferred embodiments, the anthracycline base injection is a water in oil emulsion comprising mitoxantrone base, sodium chloride, ethanol, glycerol, acetic acid and from about 3% to about 10% of water.

In certain preferred embodiments, the anthracycline base is doxorubicin base and the biocompatible carrier for injection is a mixture of oleic acid, ethanol and acetic acid.

In certain preferred embodiments, the anthracycline base injection is a solution or suspension comprising doxorubicin base, ethanol, oleic acid and acetic acid.

In certain preferred embodiments, the anthracycline base injection is a water in oil emulsion comprising doxorubicin base, sodium chloride, ethanol, oleic acid, acetic acid and from about 3% to about 15% of water.

In certain preferred embodiments, the formulation is a water in oil emulsion comprising doxorubicin base, oleic acid, ethanol, acetic acid, NACL and from about 4% to about 15% of water by volume of the emulsion.

In certain preferred embodiments, the anthracycline base injection is a water in oil emulsion comprising amrubicin base, sodium chloride, ethanol, oleic acid, acetic acid and from about 3% to about 10% of water.

In certain preferred embodiments, the vinca alkaloid base is vinblastine base and the biocompatible carrier for injection is a mixture of ethanol, a median chain triglyceride and acetic acid.

In certain preferred embodiments, the vinca alkaloid base is vinblastine base and the biocompatible carrier for injection is a mixture of ethanol, oleic acid and acetic acid.

In certain preferred embodiments, the vinca alkaloid base is vinblastine base and the biocompatible carrier for injection is a mixture of ethanol, glycerol and acetic acid.

In certain preferred embodiments, the vinca alkaloid base injection is a solution or suspension comprising vinblastine, ethanol, oleic acid and acetic acid.

In certain preferred embodiments, the vinca alkaloid base injection is a water in oil emulsion comprising vinblastine base, sodium sulfate, ethanol, oleic acid, acetic acid and from about 1% to about 10% of water.

In certain preferred embodiments, the vinca alkaloid base injection is a water in oil emulsion comprising vinblastine base, potassium sulfate, ethanol, oleic acid, acetic acid and from about 1% to about 10% of water.

In certain preferred embodiments, the vinca alkaloid base is vincristine base and the biocompatible carrier for injection is a vegetable oil.

In certain preferred embodiments, the vinca alkaloid base is vincristine base and the biocompatible carrier for injection is a mixture of ethanol, a median chain triglyceride and acetic acid.

In certain preferred embodiments, the vinca alkaloid base injection is a water in oil emulsion comprising vincristine base, sodium sulfate, ethanol, oleic acid, acetic acid and from about 1% to about 10% of water.

In certain preferred embodiments, the vinca alkaloid base injection is a water in oil emulsion comprising vincristine base, sodium sulfate, ethanol, glycerol, acetic acid and from about 1% to about 10% of water.

In certain preferred embodiments, the vinca alkaloid base injection is a water in oil emulsion comprising vincristine base, sodium sulfate, ethanol, a median chain triglyceride, acetic acid and from about 1% to about 10% of water.

In certain preferred embodiments, the vinca alkaloid base is vindesine base and the biocompatible carrier for injection is a mixture of ethanol, a median chain triglyceride and acetic acid.

In certain preferred embodiments, the vinca alkaloid base is vindesine base and the biocompatible carrier for injection is a mixture of glycerol, ethanol and acetic acid.

In certain preferred embodiments, the vinca alkaloid base is vindesine base and the biocompatible carrier for injection is a mixture of ethanol with oleic acid.

In certain preferred embodiments, the vinca alkaloid base injection is a solution or suspension comprising vindesine base, ethanol, oleic acid and acetic acid, and does not contain water.

In certain preferred embodiments, the vinca alkaloid base injection is a water in oil emulsion comprising vindesine base, sodium sulfate, ethanol, oleic acid, acetic acid and 1% to about 10% of water.

In certain preferred embodiments, the vinca alkaloid base injection is a water in oil emulsion comprising vindesine base, sodium sulfate, ethanol, glycerol, acetic acid and from about 1% to about 10% of water.

In certain preferred embodiments, the vinca alkaloid base injection is a water in oil emulsion comprising vindesine base, sodium sulfate, ethanol, a median chain triglyceride, acetic acid and from about 1% to about 10% of water.

In certain preferred embodiments, the vinca alkaloid base injection is a water in oil emulsion comprising vinblastine base, sodium sulfate, ethanol, oleic acid, acetic acid and 1% to about 10% of water.

In certain preferred embodiments, the vinca alkaloid base injection is a water in oil emulsion comprising vinblastine base, sodium sulfate, ethanol, glycerol, acetic acid and from about 1% to about 10% of water.

In certain preferred embodiments, the vinca alkaloid base injection is a water in oil emulsion comprising vinblastine base, sodium sulfate, ethanol, a median chain triglyceride, acetic acid and from about 1% to about 10% of water.

In certain preferred embodiments, the alkylating agent base is mechlorethamine base and the biocompatible carrier for injection is a mixture of ethanol and PEG having a molecular weight from about $PEG_{200}$ to about $PEG_{400}$ with acetic acid.

In certain preferred embodiments, the alkylating agent base is mechlorethamine base and the biocompatible carrier for injection is a mixture of ethanol and a median chain triglyceride with acetic acid.

In certain preferred embodiments, the alkylating agent base is mechlorethamine base and the biocompatible carrier for injection is a mixture of glycerol with ethanol.

In certain preferred embodiments, the alkylating agent base injection is a water in oil emulsion comprising mechlorethamine base, sodium chloride, ethanol, a median chain triglyceride, acetic acid and from about 0.1% to about 5% of water.

In certain preferred embodiments, the alkylating agent base injection is a water in oil emulsion comprising mechlorethamine base, sodium chloride, ethanol, a PEG of molecular mass of 200 to 400, acetic acid and from about 0.1% to about 5% of water.

In certain preferred embodiments, the alkylating agent base is bendamustine base and the biocompatible carrier for injection is a PEG having a molecular weight from about $PEG_{200}$ to about $PEG_{400}$, with the amount of PEG contained in the injection in the range of from about 30% to about 80% of the volume of the injection.

In certain preferred embodiments, the alkylating agent base is bendamustine base and the biocompatible carrier for injection is a mixture of ethanol and oleic acid.

In certain preferred embodiments, the alkylating agent base is bendamustine base and the biocompatible carrier for injection is a mixture of ethanol and glycerol.

In certain preferred embodiments, the alkylating agent base injection is a water in oil emulsion comprising bendamustine base, sodium chloride, ethanol, a PEG of molecular mass of 200 to 400, acetic acid and from about 2% to about 10% of water.

In certain preferred embodiments, the alkylating agent base injection is a water in oil emulsion comprising bendamustine base, sodium chloride, ethanol, oleic acid, acetic acid and from about 2% to about 10% of water.

In certain preferred embodiments, the alkylating agent base injection is a water in oil emulsion comprising bendamustine base, sodium chloride, ethanol, glycerol, acetic acid and from about 2% to about 10% of water.

In certain preferred embodiments, the eribulin base injection is a water in oil emulsion comprising eribulin base, sodium chloride, ethanol, oleic acid, median chain triglyceride, glycerol, a PEG of molecular weight of 200 to 400, acetic acid and from about 2% to about 10% of water.

The invention is further directed, in part, to a method of treating a malignant mass in a mammal, comprising administering an injectable formulation comprising a drug consisting of an effective amount of anthracycline base, wherein the drug is dissolved or suspended in a pharmaceutically acceptable biocompatible carrier directly into the malignant mass.

The invention is further directed, in part, to a method of treating a malignant mass in a mammal, comprising administering an injectable formulation comprising a drug consisting of an effective amount of chemotherapeutic base such as an anthracycline base, eribulin base, an alkylating agent base or a vinca alkaloid base, wherein the drug is dissolved in a pharmaceutically acceptable biocompatible carrier to form a solution or form a water in oil emulsion, wherein the formulation is directly injected into a malignant mass of a patient.

In certain embodiments of the present invention, the injectable formulation is administered through a syringe or a needle of a fiberscope.

In certain preferred embodiments of the present invention, the anthracycline base is selected from a group consisting of doxorubicin base, epirubicin base, daunorubicin base, amrubicin base or mitoxantrone base.

In certain embodiments, the malignant mass is in a location in the mammal selected from the group consisting of brain, head, eye, nasopharynx, mouth, tongue, neck, thyroid, gastrointestinal system, liver, pancreas, gall bladder, lung, respiratory system, urogenital system, kidney, urinary bladder, ovary, uterus, vagina, penis, testis, breast, lymphatic system, skin, cardiovascular system, nervous system, thorax, pleural membrane, mesothelioma, muscular skeletal system, abdomen with primary or secondary nature. In certain embodiments, the malignant mass is primary or secondary in nature in the mammal.

In certain preferred embodiments, the biocompatible carrier is a combination of PEG, oleic acid, glycerol and ethanol.

In certain preferred embodiments, the biocompatible carrier is a combination of PEG, oleic acid, glycerol, a median chain triglyceride and ethanol.

In certain preferred methods of the present invention, the anthracycline base is mitoxantrone base and the biocompatible carrier for injection is ethanol.

In certain preferred methods of the present invention, the anthracycline base is mitoxantrone base and the biocompatible carrier for injection is a PEG having a molecular weight from about $PEG_{200}$ to about $PEG_{400}$.

In certain preferred methods of the present invention, the anthracycline base is mitoxantrone base and the biocompatible carrier for injection is a mixture of a PEG having a molecular weight of from about $PEG_{200}$ to about $PEG_{400}$ and ethanol.

In certain preferred methods of the present invention, the anthracycline base is mitoxantrone base and the biocompatible carrier for injection is a mixture of oleic acid and acetic acid.

In certain preferred methods of the present invention, the anthracycline base is mitoxantrone base and the biocompatible carrier for injection is a mixture of oleic acid and ethanol.

In certain preferred methods of the present invention, the malignant mass is:
(i) a superficial malignant disease of skin, eye, tongue, mouth, thyroid, breast, cervix, uterus, anus, prostate, vagina, sarcoma of the bone, carcinoma of urethra, penis, testis and epididymis and the anthracycline base is injected with a syringe directly into the malignant mass without dilution; or
(ii) a cancer of the nasopharynx, and the anthracycline base is injected into the malignant mass with the syringe or needle through a nasopharyngoscope; or
(iii) a cancer of the liver, kidney and gall bladder, and the anthracycline base is injected using a syringe through skin into the malignant mass with the assistance of ultrasound, or is injected through a hole made in an abdominal wall of a patient during laparoscopic surgery into the malignant mass; or
(iv) a cancer of the ovary, oviduct, pancreas, metastasis of lymph node or direct peritoneum invasion of the abdominal cavity, lymphoma of the abdomen, and the anthracycline base is injected with the syringe into the malignant mass through a hole made in the abdominal wall of a patient during laparoscopic surgery; or
(v) a carcinoma or sarcoma of esophagus, stomach, duodenum, small intestine, and the anthracycline base is injected with the needle into the malignant mass through an enteroscope or via a long syringe through a hole made in the abdominal wall of a patient during laparoscopic surgery or is injected through a hole made in a thoracic wall of a patient during thoracoscopic surgery.
(vi) a carcinoma or sarcoma of the large intestine and rectum, and the anthracycline base is injected with the needle into the malignant mass through colonoscopy or is injected using a syringe through a hole made in the abdominal wall of a patient during laparoscopic surgery; or
(vii) a carcinoma or sarcoma of the lung and trachea, and the anthracycline base is injected using the needle of a fiber bronchoscope into the malignant mass; or
(viii) a carcinoma of the lung, and the anthracycline base is injected with the syringe through the thoracic wall with the use of ultrasound, x-ray, CT scan, or MR scan or is injected through a hole made in the thoracic wall of a patient during thoracoscopic surgery; or
(ix) a carcinoma or sarcoma of the urinary bladder, and the anthracycline base is injected into the malignant mass with a needle through a cystoscope, or is injected through a hole made in the abdominal wall of a patient during laparoscopic surgery; or
(x) a carcinoma or sarcoma of uterus, and the injectable formulation of the anthracycline base is injected into the malignant mass with a syringe or a needle of a hysteroscope; or is injected through a hole made in the abdominal wall of a patient during laparoscopic surgery; or
(xi) a carcinoma or sarcoma of nasopharynx and larynx, and the anthracycline base is injected into the malignant mass with a needle through a laryngoscope; or
(xii) a carcinoma of the brain, and the anthracycline base is injected with a needle of a syringe or a fiberscope into the malignant mass after a hole is drilled in the corresponding bone of a skull with the use of an X-ray, CT scan or MR scan; or
(xiii) a malignant lymphoma or lymph node with metastasis, and the anthracycline base is injected into the malignant mass using a needle through the skin of a patient or is injected through a hole made in the abdominal wall of a patient during laparoscopic surgery or through a hole made in the thoracic wall of a patient during thoracoscopic surgery.

The invention is further directed to a kit, comprising a first vial containing a drug consisting of a powdered or lyophilized anthracycline base and a second vial containing the pharmaceutically acceptable excipients needed to deliver the anthracycline base to a tumor, the pharmaceutically acceptable excipient comprising a PEG having a molecular weight from about $PEG_{200}$ to about $PEG_{400}$, an oleic acid, glycerol, an alcohol selected from ethanol, propylene glycol, benzyl alcohol, tert-butyl alcohol or a combination thereof. In other embodiments the pharmaceutically acceptable excipient comprises a combination of an alcohol with PEG. In certain preferred embodiments, the pharmaceutically acceptable excipient comprises PEG, oleic acid, glycerol and ethanol.

The invention is further directed to a kit, comprising a first vial containing a drug consisting of a powdered or liquid chemotherapeutic base comprising an anthracycline base, vinca alkaloid base, eribulin base or alkylating agent base and a second vial containing the pharmaceutically acceptable excipients needed to deliver the chemotherapeutic base into a tumor, the pharmaceutically acceptable excipient comprising a PEG having a molecular weight from about $PEG_{200}$ to about $PEG_{400}$, a median chain triglyceride, glycerol, an oleic acid, vegetable oil, an alcohol selected from ethanol, benzyl alcohol or a combination thereof. In certain preferred embodiments, the pharmaceutically acceptable excipient comprises a mixture of ethanol with a PEG or an oleic acid, a median chain triglyceride, vegetable oil and glycerol. The alcohol was used to reduce the viscosity of the injection.

The invention is further directed to intratumor injectable formulation kit, comprising a first vial containing a basic chemotherapeutic drug and a second vial containing a pharmaceutically acceptable excipient for delivery of the drug into a tumor, the pharmaceutically acceptable excipient comprising a solvent selected from the group consisting of PEG, an oleic acid, glycerin, a median chain triglyceride, an alcohol, a pharmaceutically acceptable diluent, and mixtures thereof, wherein the PEG has a molecular weight from about $PEG_{200}$ to about $PEG_{400}$, and wherein the alcohol is selected from the group consisting of ethanol, propylene glycol, tert-butyl alcohol, benzyl alcohol and combinations thereof; and wherein the basic chemotherapeutic drug is selected from the group consisting of an anthracycline base, a vinca alkaloid base, eribulin base and an alkylating agent base. In certain embodiments, the anthracycline base is selected from the group consisting of doxorubicin base, epirubicin base, daunorubicin base, amrubicin base and mitoxantrone base, and wherein the pharmaceutical comprises an alcohol selected from the group consisting of ethanol, benzyl alcohol and combinations thereof comprises an alcohol selected from the group consisting of ethanol, benzyl alcohol and combinations thereof comprises an alcohol selected from the group consisting of ethanol, benzyl alcohol and combinations thereof acceptable excipient comprises a mixture of ethanol and oleic acid, PEG, polysorbate, a median chain triglyceride or glycerol.

In other embodiments, the injectable formulation contains alcohol. In still other embodiments, the injectable formulation does not contain any alcohol. In certain preferred embodiments, the injectable composition is for direct injection into local cancer tissue, and is not intended for venous injection. In other embodiments, the injectable composition further contains one or more pharmaceutically acceptable excipients, such as, but not limited to, ethyl oleate, benzyl benzoate, polysorbate, PEG, cholesterol, phospholipid, propylene glycol, glycerin, ethyl alcohol, niacinamide, dimethyl sulfoxide, dimethylacetamide, surfactants (e.g., nonionic surfactants), etc.

In certain preferred embodiments, the anthracycline base is one of the following: doxorubicin base, daunorubicin base, epirubicin base, pirarubicin base, valrubicin base, aclarubicin base, idarubicin base, amrubicin and mitoxantrone base.

In certain preferred embodiments, the vinca alkaloid base is one of the following: vinblastine base, vincristine base and vindesine base.

In certain preferred embodiments, the alkylating agent base is one of the following: mechlorethamine base and bendamustine base.

The invention is further directed to a method of treating a malignant mass in a mammal, comprising administering the intratumor injectable formulation of claim 1 directly into the malignant mass, wherein the malignant mass is a primary or secondary tumor located in skin, eye, tongue, mouth, thyroid, breast, cervix, uterus, anus, prostate, vagina, sarcoma of the bone, urinary bladder, ureter, urethra, penis, testis, epididymis, nasopharynx, liver, kidney, gall bladder, ovary, oviduct, pancreas, metastasis of lymph node, peritoneum metastasis of the abdominal cavity, esophagus, stomach, duodenum, small intestine, large intestine, caecum, rectum, lung, trachea, larynx, brain, a malignant lymphoma or lymph node metastasis, metastatic breast cancer, metastatic Wilms' tumor, Kaposi's sarcoma, metastatic neuroblastoma or metastatic soft tissue sarcoma.

The invention is also directed to a method of making an intratumor injectable formulation comprising dissolving a basic chemotherapeutic drug selected from the group consisting of an anthracycline base, eribulin base, a vinca alkaloid base, and an alkylating agent base in an organic liquid comprising a solvent selected from the group consisting of a PEG of molecular weight of 200 to 400, a median chain triglyceride, oleic acid, glycerol, a liquid alcohol and mixtures thereof. In certain embodiments, the intratumor injectable formulation is a solution or suspension. In other embodiments, the intratumor injectable formulation is an emulsion.

The invention is also directed to a method of making an intratumor injectable emulsion formulation comprising: 1) the acidic salt of a chemotherapeutic drug selected from the group consisting of a vinca alkaloid salt, an alkylating agent salt, an eribulin salt and an anthracycline salt with an about equal molar amount of a base or a basic salt in an aqueous medium to form a water suspension of a basic chemotherapeutic drug; 2) adding a small amount of an organic acid selected from the group consisting of acetic acid, malic acid, fumaric acid, tartaric acid, succinic acid, maleic acid, citric acid, ascorbic acid and combinations thereof into the suspension to act as a buffer; 3) mixing the resulting desalinated basic chemotherapeutic water mixture with a biocompatible carrier selected from the group consisting of a PEG of molecular weight of 200 to 400, a median chain triglyceride, oleic acid, glycerol, a liquid alcohol comprising ethanol, benzyl alcohol, and mixtures thereof, wherein the emulsion comprises an amount of water from about 0.5% to about 15% of the total volume of the injectable formulation. In certain embodiments, wherein the vinca alkaloid salt is selected from the group consisting of vinblastine sulfate, vinblastine chloride, vincristine sulfate, vincristine chloride, vindesine sulfate, and vindesine chloride, wherein the anthracycline salt is selected from the group consisting of doxorubicin hydrochloride, doxorubicin sulfate, doxorubicin citrate, epirubicin hydrochloride, epirubicin sulfate, epirubicin citrate, daunorubicin hydrochloride, daunorubicin sulfate daunorubicin citrate, mitoxantrone hydrochloride, mitoxantrone sulfate, mitoxantrone citrate, amrubicin hydrochloride, amrubicin sulfate, amrubicin citrate, idarubicin salt, aclarubicin salt and valrubicin salt; and wherein the alkylating agent salt is selected from the group consisting of bendamustine hydrochloride, bendamustine sulfate, mechlorethamine hydrochloride, mechlorethamine sulfate, procarbazine hydrochloride, and procarbazine sulfate.

The invention is additionally directed to a method of making an intratumor injectable water in oil emulsion comprising dissolving the acidic salt of a chemotherapeutic drug in water in an amount of less than 15% of the total volume of the injectable emulsion; desalinating the salt form of a chemotherapeutic drug selected from the group consisting of a vinca alkaloid salt, an alkylating agent salt, eribulin salt and an anthracycline salt with an about equal molar base or basic salt in an aqueous medium to form a basic chemotherapeutic drug of water suspension; a small amount of organic acid comprising acetic acid, malic acid, fumaric acid, tartaric acid, succinic acid, maleic acid, citric acid, ascorbic acid was added into the suspension to act as a buffer, to form a desalinated chemotherapeutic drug mixture; mixing the resulting desalinated basic chemotherapeutic drug mixture with a biocompatible carrier selected from the group consisting of a PEG of molecular weight of 200 to 400, a median chain triglyceride, oleic acid, glycerol, a liquid alcohol comprising ethanol and/or benzyl alcohol and mixtures thereof; wherein the formulation is an emulsion. In certain embodiments, vinca alkaloid salt is selected from the group consisting of vinblastine salt (e.g. vinblastine sulfate), vincristine salt (e.g. vincristine sulfate), and vindesine salt (e.g. vindesine sulfate); wherein the anthracycline salt is selected from the group consisting of doxorubicin salt (e.g. doxorubicin hydrochloride), epirubicin salt (e.g epirubicin hydrochloride), daunorubicin salt (e.g. daunorubicin hydrochloride), mitoxantrone salt (e.g. mitoxantrone hydrochloride), idarubicin salt (e.g. idarubicin hydrochloride), amrubicin salt, aclarubicin salt (e.g. aclarbucin hydrochloride) and valrubicin salt (e.g. valrubicinw hydrochloride); and wherein the alkylating agent salt is selected from the group consisting of bendamustine salt (e.g. bendamustine hydrochloride), mechlorethamine salt (e.g. mechlorethamine hydrochloride) and procarbazine salt (e.g. procarbazine hydrochloride).

In order for the invention described herein to be more fully understood, the following definitions are provided for the purposes of this disclosure.

The term "patient" broadly refers to any animal that is to be treated with the formulation and by the methods herein disclosed. The present formulations and methods can provide treatment to any animal, e.g., any vertebrate, including but not limited to humans (preferred embodiments), primates, dogs, cats, horses, cattle, etc. In preferred embodiments, the patient is a human. The patient (such as human) may have advanced disease or lesser extent of disease, such as low tumor burden. In some embodiments, the patient is at an early stage of a proliferative disease (such as cancer). In other embodiments, the patient is at an advanced stage of a proliferative disease (such as an advanced cancer).

As used herein, the term "unit dose" refers to physically discrete units suitable as unitary dosages for mammalian subjects.

The term "comprising" is an inclusive term interpreted to mean containing, embracing, covering or including the elements listed following the term, but not excluding other unrecited elements.

A "therapeutically effective amount" means the amount that, when administered to an animal for treating a disease, is sufficient to produce a desired therapeutic effect (e.g. to affect treatment for that disease).

As used herein, the term "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The terms "composition" and "formulation" are used interchangeably herein.

BRIEF DESCRIPTION OF THE DRAWINGS

FIG. 1 is a graphical depiction of an intensity-weighted NICOMP distribution analysis.

DETAILED DESCRIPTION OF THE INVENTION

The invention will be described with reference to various specific and preferred embodiments and techniques. However, it should be understood that many variations and modifications can be made while remaining with the spirit and scope of the invention.

In current practice, the standard treatment of most advanced solid tumors is surgical removal often followed by chemotherapy. However, this treatment is often unsuccessful, and the chemotherapy is often limited by the side effects caused by such agents (as previously explained above).

Chemotherapeutic Agents

A chemotherapeutic agent injected into a vein or an artery of the patient with cancer can be carried away from the tumor without entering into the cancer cell, and therefore the efficacy (e.g., cell-killing effect) is weak. In contrast, when a lipid-dissolved chemotherapeutic agent is directly injected into a tumor, it can exert its effect over a longer duration and can enter the cancer cell more easily.

Examples of chemotherapeutic agents useful in the formulations of the present invention include an anthracycline base, an alkylating agent base, eribulin base or a vinca alkaloid base, all of which is water insoluble and is different from its hydrochloride salt, mesylate or a sulfate salt. Such a chemotherapeutic base injection, (e.g. an anthracycline base injection, an alkylating base injection or a vinca alkaloid base injection) has not previously been considered for use in injectable formulations or, more specifically for the contemplated local injection into a tumor.

Preferably, the anthracycline base comprises doxorubicin base, daunorubicin base, epirubicin base, mitoxantrone base, amrubicin base, pirarubicin base, valrubicin base, idarubicin base and aclarubicin base. Preferably, the alkylating agent base comprises mechlorethamine base and bendamustine base.

Preferably, the vinca alkaloid base comprises vinblastine base, vincristine base and vindesine base.

Administration of Formulation

The chemotherapeutic base including an anthracycline base, eribulin base, a vinca alkaloid base or an alkylating agent base used in the injectable formulations and treatments of the present invention are preferably dosed in therapeutically effective amounts known to those skilled in the art. In certain embodiments, the therapeutically effective amount is an amount that yields a maximum therapeutic effect. In other embodiments, the therapeutically effective amount yields a therapeutic effect that is less than the maximum therapeutic effect. For example, a therapeutically effective amount may be an amount that produces a therapeutic effect while avoiding one or more side effects associated with a dosage that yields maximum therapeutic effect. One skilled in the clinical and pharmacological arts will be able to determine a therapeutically effective amount through routine experimentation, namely by monitoring a subject's response to administration of the agent and adjusting the dosage accordingly. For additional guidance, see, e.g., Remington: The Science and Practice of Pharmacy, 22$^{nd}$ Edition, Pharmaceutical Press, London, 2012, and Goodman & Gilman's The Pharmacological Basis of Therapeutics, 12$^{th}$ Edition, McGraw-Hill, New York, N.Y., 2011, the entire disclosures of which are incorporated by reference herein.

TABLE 1

Suggested Dosage:

| Anthracycline base | Diameter of tumor (cm) | Dosage of the drug (mg)/week | Approximate Vol. of anthracycline injected(ml) | Conc. mg/ml |
|---|---|---|---|---|
| Doxorubicin | 8 | 32-240 | 265 cm$^3$ × 0.06 = 16 | 2-15 |
|  | 5 | 8-60 | 65 cm$^3$ × 0.06 = 3.9 |  |
|  | 2-3 | 0.5-3.75 | 4.2 cm$^3$ × 0.06 = 0.25 |  |
| Epirubicin | 8 | 32-240 mg | 265 cm$^3$ × 0.06 = 16 | 2-15 |
|  | 5 | 8-60 | 65 cm$^3$ × 0.06 = 3.9 |  |
|  | 2-3 | 0.5-3.75 | 4.2 cm$^3$ × 0.06 = 0.25 |  |
| Daunorubicin | 8 | 32-240 mg | 265 cm$^3$ × 0.06 = 16 | 2-15 |
|  | 5 | 8-60 | 65 cm$^3$ × 0.06 = 3.9 |  |
|  | 2-3 | 0.5-3.75 | 4.2 cm$^3$ × 0.06 = 0.25 |  |
| Mitoxantrone | 8 | 8-32 | 265 cm$^3$ × 0.06 = 16 | 0.5-2 |
|  | 5 | 2-8 | 65 cm$^3$ × 0.06 = 3.9 |  |
|  | 2-3 | 0.12-0.5 | 4.2 cm$^3$ × 0.06 = 0.25 |  |

Doxorubicin Hydrochloride Liposome Injection is approved for the treatment of patients with ovarian cancer whose disease has progressed or recurred after platinum-based chemotherapy, AIDS-related Kaposi's sarcoma in patients after failure of prior systemic chemotherapy or intolerance to such therapy and multiple myeloma. Doxorubicin hydrochloride liposome injection can cause myocardial damage with the risk of cardiomyopathy being 11% when the cumulative anthracycline dose was between 450 mg/m$^2$ to 550 mg/m$^2$. Serious, life-threatening, and fatal infusion-related reactions can occur with doxorubicin hydrochloride liposome injection. Acute infusion-related reactions occurred in 11% of patients with solid tumors.

As noted above, potential applications of the formulations of the invention include direct administration (e.g., injection) into a malignant cancer or sarcoma mass in the body. In certain embodiments, potential treatment sites include, but are not limited to, the following cancers or tumors: a hepatocellular carcinoma, a metastatic cancer of the liver, an advanced hepatocellular carcinoma, a pancreatic cancer, an adenocarcinoma, a mastocytoma or a mast cell tumor, an ovarian cancer, a non-small cell lung cancer, a small cell lung cancer, melanoma, retinoblastoma, breast tumor, colorectal carcinoma, a histiocytic sarcoma, a brain tumor, an astrocytoma, a glioblastoma, a neuroma, a neuroblastoma, a colon carcinoma, cervical carcinoma, sarcoma of any organ, prostate tumor, bladder tumor, tumor of the reticuloendothelial tissues, Wilm's tumor, Kaposi's sarcoma, a cancer, or an osteosarcoma of bone, a renal cancer, or head and neck cancer, oral cancer, a laryngeal cancer, or an oropharyngeal cancer, breast cancer, genitourinary cancer, gastrointestinal cancer, epidermoid cancer, melanoma and metastasis to bone. In a broader sense of the invention, the formulations and treatments of the invention may be used to treat a proliferative disease selected from hyperproliferative conditions such as hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty. In certain embodiments, the formulations and treatments are used with respect to gastrointestinal cancers other than pancreatic cancer. In some embodiments, the proliferative disease is cancer. In some embodiments, the proliferative disease is a non-cancerous disease. In some embodiments, the proliferative disease is a benign or malignant tumor, and encompasses metastasis in the original organ or tissue and/or in any other location of the tumor. In some embodiments, there is provided a method of treating a primary tumor. In some embodiments, there is provided a method of treating cancer that has metastasized from the primary tumor. In some embodiments, there is provided a method of treating cancer at advanced stage(s). In some embodiments, there is provided a method of treating breast cancer (HER2 positive or HER2 negative), including, for example, advanced breast cancer, stage IV breast cancer, locally advanced breast cancer, and metastatic breast cancer. In some embodiments, there is provided a method of treating lung cancer, including, for example, non-small cell lung cancer (NSCLC, such as advanced NSCLC), small cell lung cancer (SCLC, such as advanced SCLC), and advanced solid tumor malignancy in the lung. In some embodiments, there is provided a method of treating any of ovarian cancer, head and neck cancer, gastric malignancies, melanoma (including metastatic melanoma), colorectal cancer, pancreatic cancer, and solid tumors (such as advanced solid tumors).

In the methods of the invention, the chemotherapeutic agent is preferably administered directly into the malignant mass of the cancer or sarcoma of the body via (direct) injection. For superficial malignant disease of skin, eye, tongue, mouth, thyroid, breast, cervix, uterus, anus, prostate, penis, vagina, sarcoma of the bone, carcinoma of urethra, etc., the basic chemotherapeutic drug such as an anthracycline base, eribulin base, a vinca alkaloid base or an alkylating agent base can be injected with the syringe directly into the malignant mass without dilution.

In certain embodiments of the invention, the injectable formulation of the invention is injected with a syringe directly into a malignant mass. This embodiment is particularly useful, e.g., for cancer of the liver, kidney, gall bladder, ovary, oviduct, pancreas, metastasis of lymph node or direct peritoneum invasion of the abdominal cavity through the hole of laparoscopic surgery.

In certain embodiments of the invention, the injectable formulation of the invention is injected into the malignant mass with a syringe or needle through a nasopharyngoscope. This embodiment is particularly useful, e.g., for a cancer of the nasopharynx.

In certain embodiments of the invention, the injectable formulation of the invention is injected using a syringe through the skin into the malignant mass with the assistance of ultrasound. This embodiment is particularly useful, e.g., for cancer of the liver, kidney and gall bladder.

In certain embodiments of the invention, the injectable formulation of the invention is injected laparoscopically with a needle into the malignant mass. This embodiment is particularly useful, e.g., for cancer of the ovary, oviduct, pancreas, metastasis of lymph node or direct peritoneum invasion of the abdominal cavity.

In certain embodiments of the invention, the injectable formulation of the invention is injected into the malignant mass through an enteroscope or via combination therapy with a laparoscopic or thoracoscopic surgery. This embodiment is particularly useful, e.g., for a carcinoma or sarcoma of esophagus, stomach, duodenum, and/or small intestine.

In certain embodiments of the invention, the injectable formulation of the invention is injected with a needle into the malignant mass through colonoscopy or combination therapy with the laparoscopic surgery. This embodiment is particularly useful to treat, e.g., a carcinoma or sarcoma of large intestine and/or rectum.

In certain embodiments of the invention, the injectable formulation of the invention is injected with a needle of a fiber bronchoscope into the malignant mass. This embodiment is particularly useful to treat, e.g., a carcinoma or sarcoma of the throat, lung and/or trachea.

In certain embodiments of the invention, the injectable formulation of the invention is injected with a syringe under the help of ultrasound, x-ray, CT scan, MR scan or via the hole of a thoracic wall of thoracoscopic surgery. This embodiment is particularly useful to treat, e.g., a carcinoma of the lung and thorax, lymphoma of the thorax or lymph node metastasis in the thorax.

In certain embodiments of the invention, the injectable formulation of the invention is injected into the malignant mass with a needle through a cystoscope, or through the hole made in the abdominal wall during laparoscopic surgery. This embodiment is particularly useful to treat, e.g., a carcinoma or sarcoma of the urinary bladder.

In certain embodiments of the invention, the injectable formulation of the invention is injected into the malignant mass with a syringe or a needle via a hysteroscope. This embodiment is particularly useful to treat, e.g., a carcinoma or sarcoma of the uterus, a carcinoma of the cervix, a endometrial carcinoma.

In certain embodiments of the invention, the injectable formulation of the invention is injected into the malignant mass with a needle through a laryngoscope. This embodiment is particularly useful to treat, e.g., a carcinoma or sarcoma of the pharynx and/or larynx.

In certain embodiments of the invention, the injectable formulation of the invention is injected with the needle into the malignant mass after a hole is drilled in the corresponding bone of the skull under the help of fiber scope, X-ray, CT scan or MR scan. This embodiment is particularly useful to treat, e.g., a carcinoma of the brain.

One skilled in the art will appreciate that the doses for the cancer or sarcoma of different organs is dependent on the size or volume of the mass to be treated.

One skilled in the art will appreciate that the time interval between 2 local injection of the cancer or sarcoma of different organs is dependent on the doubling time of the growth of the mass of tumor to be treated.

In certain preferred embodiments, the formulation comprises a therapeutically effective dose (e.g., about 38 mg) of doxorubicin base in about 20 ml of pharmaceutically acceptable carrier (e.g., $PEG_{300}$). In general, the dosage is from about 1 to about 10 ml of the solution or suspension, depending on the size or volume of the mass. The volume of the drug used preferably should be smaller than about 6% of the mass; otherwise the liquid will flow out of the injection site. In certain embodiments, the tumor is injected with drug once a week. The number of injections and the time between injections is within the knowledge of those skilled in the art, and is dependent in part on the size or volume of the tumor. In certain embodiments, the time between two injections is about one week.

In certain preferred embodiments, the formulation comprises 15 mg per ml of daunorubicin base and the pharmaceutically acceptable carrier is a mixture of oleic acid and ethanol with acetic acid and sodium hydroxide as the buffer. In general, the dosage is from about 1 to about 10 ml of the solution, suspension or emulsion depending on the size or volume of the mass. The volume of the drug used preferably should be smaller than 6% of the mass; otherwise the liquid will flow out of the injection site. In certain embodiments, the tumor is injected with drug once a week. In another embodiment, the tumor is injected every four days. The number of injections, the time between injections and the concentration of the injection depends on the size of the tumor and the type of the tumor, which is within the knowledge of those skilled in the art. In certain embodiments, the time between two injections is about one week. In other embodiment the time between 2 injections of 2 cycles of treatment is from about 4 to about 10 days. Some cancer has shorter doubling time, therefore the interval of injection may be 4 days or shorter.

In certain embodiments, the injectable formulation is administered by using a fiberscope, particularly in places that are hard to reach via injection. The use of a fiberscope is considered minimally invasive surgery. It is contemplated that the basic chemotherapeutic agent (e.g. anthracycline base, vinca alkaloid base or alkylating agent base) can be administered to a tumor within the intracerebral, intrathoracic or intraperitoneal cavity through the use of a fiberscope, a syringe of a laparoscope, thoracoscope or other medical instrument. For example, in certain embodiments wherein the primary tumor has metastasized, the injectable formulations of the present invention are administered to both the primary malignant mass and any secondary tumors.

The methods of the present invention enable killing of cancer cells without harm to normal cells (which occurs when the chemotherapeutic agent is systemically administered) with less trauma to the patient. The direct injection of the basic chemotherapeutic agent (e.g. anthracycline base, vinca alkaloid base or alkylating agent base) into the malignancy also greatly reduces or eliminates many common side effects. For example, replacing surgery with direct injection of the e.g. daunorubicin base into the malignancy prevents disfigurement of the face of a patient with carcinoma of tongue or mouth, the loss of a breast in a patient with breast cancer, amputation of a leg in a patient with sarcoma of the bone and loss of the uterus of a patient with cancer of cervix or early stage cancer of the uterus. Direct injection of the anthracycline base, eribulin base, vinca alkaloid base or basic alkylating drug into a malignancy also reduces or eliminates side effects such as myelosuppression, neurotoxicity, lung injury, pulmonary fibrosis, acute cardiotoxicity, heart failure, intracardiac conduction disorders and arrhythmias, gastrointestinal reactions, and/or alopecia.

Cancer 'seeds' grow in certain selected sites only ('soil') as hypothesized in the soil and seed hypothesis of cancer metastasis. If the metastasis and the primary mass of a malignancy is small, it cannot threaten the life of patient. If the tumor is large, it can be detected easily with the help of a CT scan or MR scan or fiberscope. With the assistance of a fiberscope and/or laparoscope, formulations of the present invention (containing e.g. an anthracycline base, a vinca alkaloid base or a basic alkylating drug as the active ingredient) can be injected directly into a large tumor without affecting the normal (surrounding) tissue, enabling the killing of cancer cells (e.g., making the mass smaller or shrinking the tumor), delaying or stopping the growth of the malignant mass, and enabling patients with advanced cancer to live with the tumor. When the basic chemotherapeutic drug, such as an anthracycline base, a vinca alkaloid base or an alkylating agent base, is injected into the tumor, the drug flows along the blood vessel or the lymphatic vessel to the metastasis, and it kills the metastasis cell. The injection of basic chemotherapeutic drug into the tumor results in little trauma to the patient and can be repeated, e.g., many times per month.

Manufacture

The injectable formulation of the invention may be prepared for use in any of a variety of ways known to those skilled in the art. The formulation may be prepared in advance and stored until needed, in sterile form with the optional inclusion of effective amounts of preservatives. Alternatively, it may be preferable to store the basic chemotherapeutic drug in solid or liquid form and reconstitute the formulation into an injectable formulation at a time shortly before it is to be administered, i.e., one hour or less prior to use, or preferably about fifteen minutes prior to use. In such a case, the basic chemotherapeutic drug including an anthracycline base, eribulin base, a vinca alkaloid base or alkylating agent base is stored separately from the biocompatible carrier.

Prior to use, the basic chemotherapeutic agent, e.g. an anthracycline base, eribulin base, a vinca alkaloid base or an alkylating agent base, is preferably contained in a pharmaceutical acceptable carrier. Examples of pharmaceutically acceptable carriers include one or more of PEG, ethanol, glycerol, propylene glycol, tert-butyl-alcohol, oleic acid, a medium chain triglyceride, vegetable oil, polysorbate and the like, as well as combinations thereof. Pharmaceutically acceptable carriers must be compatible with both the components of the composition and the (e.g., human) patient.

In certain preferred embodiments, the formulation of the invention comprises anthracycline base together with a PEG, ethanol, glycerol, propylene glycol, tert-butyl-alcohol and oleic acid. In certain preferred embodiments, the PEG has a molecular weight from about 100 to about 400, preferably from about 200 to about 400 or preferably from about 200 to about 300 and most preferably the PEG is selected from $PEG_{200}$, $PEG_{300}$, $PEG_{400}$, and mixtures of any of the foregoing.

In certain embodiments, the anthracycline base is insoluble in water. In certain embodiments, the anthracycline base comprises daunorubicin base, doxorubicin base, epirubicin base, valrubicin base, amrubicin base, pirarubicin base, idarubicin base, mitoxantrone base, and/or aclarubicin base or combinations thereof. In such embodiments, the injectable composition preferable contains one or more organic excipients for injection that can dissolve or suspend the anthracycline base sufficiently to inject it into desired site, e.g., the malignant mass. In certain embodiments, the injectable composition does not contain other solvents. In other embodiments, the injectable formulation contains alcohol. In other embodiments, the injectable formulation does not contain any alcohol. In other embodiments, the injectable composition further contains one or more pharmaceutically acceptable excipients, such as, but not limited to, ethyl oleate, benzyl benzoate, polysorbate, PEG, oleic acid, cholesterol, phospholipid, propylene glycol, glycerin, ethyl alcohol, niacinamide, dimethyl sulfoxide, dimethylacetamide, polysorbate, surfactants (e.g., non-ionic surfactants), organic acid, etc. In certain preferred embodiments, the excipients in the injectable composition comprise PEG, oleic acid, median chain triglycerides, vegetable oil, glycerol and ethanol. In certain preferred embodiments, the injectable composition is for direct injection into local cancer tissue, and is not intended for venous injection. In certain embodiments, the injectable composition includes two or more anthracycline bases.

In certain embodiments, the concentration of the anthracycline base in the pharmaceutically acceptable solvent (carrier) for injection is from about 0.5 mg/1 ml to about 25 mg/ml. In certain preferred embodiments, the concentration of the anthracycline base in the pharmaceutically acceptable solvent (carrier) for injection is from about 5 mg/5 ml to about 25 mg/5 ml. In other preferred embodiments, the concentration of the anthracycline base in the pharmaceutically acceptable solvent (carrier) for injection is from about 5 mg/ml to about 20 mg/ml.

In certain embodiments, the injectable formulation may include a buffer. The buffer is used in an appropriate amount to adjust the pH of the formulation to an injectable range, for example about pH 3.5 to about pH 7, and preferably about pH 4 to about pH 6.0. The buffer may be, for example, sodium phosphate, disodium hydrogen phosphate, sodium dihydrogen phosphate, potassium phosphate, dipotassium hydrogen phosphate, potassium dihydrogen phosphate, sodium carbonate, sodium bicarbonate, arginine, triethanolamine, acetic acid, malic acid, fumaric acid, tartaric acid, maleic acid, succinic acid and citric acid. The injectable formulation may contain two or more buffers.

In certain embodiments, the injectable formulation may include an isotonic agent to adjust the osmotic pressure of the present formulation to an injectable range. The isotonic agent may be, for example, sodium chloride, and D-mannitol. Preferably, the isotonic agent is D-mannitol. In other preferred embodiments of the invention, the isotonic agent is sodium chloride.

In certain embodiments of the present invention, the injectable formulation of the present invention is premixed and stored in a pharmaceutically acceptable container (e.g., a vial) for later use. In such embodiments, it is preferable that the injectable formulation is one that provides adequate stability in accordance with guidelines provided, e.g., by governmental regulatory authorities such as the United States Food and Drug Administration ("FDA"). In other embodiments, it is contemplated that the basic chemotherapeutic drug (e.g. an anthracycline base, a vinca alkaloid base or a basic alkylating agent) will be separately supplied and mixed together with inactive pharmaceutically acceptable ingredients such as those described herein within a short time or immediately prior to being injected into the tumor of e.g., a human patient. In such embodiments, the basic chemotherapeutic drug may be stored in one container and a pharmaceutically acceptable carrier for injection stored in another container, the pharmaceutically acceptable carrier being an organic liquid. After mixing the contents of the two containers, a pharmaceutically acceptable injectable formulation is preferably formed, which in certain embodiments may be a suspension and may provide a sustained release of the anthracycline base, the vinca alkaloid base or the alkylating agent base. The injectable formulation of the invention can be administered through the following steps; i.e., from a vial filled with the present formulation, the content is transferred into an injection syringe via a needle and then administered directly into a tumor(s).

Furthermore, in certain embodiments, the present formulation may comprise one container such as a vial containing crystallized or lyophilized anthracycline base to give a powder-filled formulation. The lyophilized formulation or the powder-filled formulation can be administered by mixing the contents of that vial with a second vial that contains the pharmaceutically acceptable excipients needed to deliver the anthracycline base to the tumor. For example, the second vial may comprise an injectable liquid for the e.g. anthracycline base and the final formulation is prepared by mixing the anthracycline base of the first vial with the injectable liquid of the second vial just before use. Further, the injectable liquid of the second container may be e.g., sterilized and/or sterilized by filtration and then filled in a vial. The particles of the anthracycline base can be filled into vials and then sterilized by gamma-irradiation. The e.g. anthracycline base particles and the suspension (or solution) medium may be extemporaneously mixed so as to suspend or dissolve the chemotherapeutic particles in the vehicle for injection before administration.

In certain embodiments, the base chemotherapeutic agent is prepared by desalination of an acidic salt of the chemotherapeutic agent at the time of manufacture of the injectable formulation because many premanufactured chemotherapeutic bases are not stable. In certain other embodiments, e.g. when the chemotherapeutic agent is mitoxantrone or merchlorethamine, the basic form is stable and is preferably made before manufacture of the injectable formulation.

The injectable formulation according to the present invention may be useful for administration with a sustained-release of the anthracycline base, vinca alkaloid base or alkylating agent base for at least 1 hour, at least 3 hours, at least 4 hours, at least 5 hours, at least 6 hours, at least 12 hours, at least 24 hours, at least 30 hours, at least 36 hours, at least 48 hours or more.

The present invention relating to intratumor injection of basic chemotherapeutic agents and in particular, anthracyclines, can prevent the occurrence of the systemic side effects of intravenous injections because anthracycline base is insoluble in water and cannot be carried away from the site of injection to distant organs. Anthracycline hydrochloride injections are only useful for intravenous injections and are not appropriate for use in a malignant mass because they are not lipid soluble and cannot pass through the cell membrane of cancer cell. Anthracycline base injections are only for intra-tumor injection and are good for use in a malignant mass because they are lipid soluble and can pass through the cell membrane of cancer cell. Anthracycline hydrochloride injections contain more than 96% of water by volume, which is stable at 2-80° C. but anthracycline base injections contain no more than 15% of water by volume of the solution and are only stable when stored below −5° C.

In one method of producing the water in oil emulsion of the present invention, the acidic salt of a chemotherapeutic drug was desalinated in an aqueous medium by a basic chemical or basic salt to produce a basic chemotherapeutic drug, sodium chloride or sodium sulfate (a neutral salt), and water. The basic chemotherapeutic drug formed during desalination was then mixed with a mixture of an organic solvent such as ethanol with oleic acid, MCT, PEG, glycerol or vegetable oil. A weak acid was added to the mixture as a buffering agent to increase the solubility of the basic chemotherapeutic drug in the emulsion. Next, the aqueous solution was dispersed in the oil phase after stirring of the mixture. When the organic solvent is a weak acid, such as oleic acid.

Daunorubicin base is a deep brown powder. The daunorubicin base is different from daunorubicin hydrochloride in that it has a smaller molecular weight of 527.5 g/mol. Its molecular formula is $C_{27}H_{29}NO_{10}$. For 10 mg per ml of water, its pH is 9.3. Daunorubicin base is insoluble in water, but slightly soluble in an organic liquid such as oleic acid, PEG and ethanol. It is not stable in base form.

The daunorubicin intratumor injectable formulation of the present invention can be a solution, suspension or water in oil (W/O) type nano emulsion. In a daunorubicin intratumor injectable solution, the daunorubicin base is completely soluble in the organic solvent, which may be a mixture of ethanol with oleic acid, PEG, glycerol or other organic chemicals. In a daunorubicin intratumor injectable suspension, the daunorubicin base is incompletely soluble in the organic solvent because the concentration of the daunorubicin is too high. The daunorubicin base of the oversaturated solution is precipitated from the mixture.

The water in oil nano emulsion is manufactured by dissolving a certain amount daunorubicin hydrochloride (e.g. from about 0.3% to about 2.5%) and the same molar weight of sodium hydroxide in a sufficient amount of water (e.g. from about 4 to about 6% of the v/v of the injection in the container). The desalination base can be other such as sodium carbonate, bicarbonate, sodium acetate, potassium hydroxide, potassium acetate, potassium carbonate, bicarbonate, etc. Then a suitable amount of organic liquid, such as ethanol and oleic acid (e.g from about 90% to about 96%), is added into the container to dissolve the basic chemical produced, and a small amount of acetic acid as the buffer. The solution of the invention is then passed through a 0.22 micron filter and then about 2.2 ml of filtrate is filled into a vial under nitrogen. The concentration to produce 2 mg/ml is 0.2% and to produce 20 mg/ml is 2%.

The daunorubicin intratumor injectable water in oil nano emulsion comprises daunorubicin base (e.g. from about 0.2% to about 2.5%) dissolved in an organic solvent (e.g. from about 90% to about 96%), water (e.g. from about 4% to about 6%), oleic acid (e.g. from about 40 to about 85%), an alcohol such as ethanol or benzyl alcohol (e.g. from about 60% to about 15%), and acetic acid as buffer (e.g. from about 0.1% to about 0.5%). It is not stable when stored at room temperature for two months, but is stable when stored below −5° C. for eight months.

Another method of producing the intra tumor injection involves mixing the daunorubicin base with an alcohol and oleic acid. However, no suitable daunorubicin base is currently available for purchase on the market. If the base is manufactured before the formulation production, the process is complicated, time consuming and the resulting free base produced is not stable for a long period of time, the related matter may not comply with the requirement of the specification and may not be suitable for commercial use. Therefore, it is preferrable to produce the anthracycline base during production of the formulation.

The intratumor injectable formulation may comprise a kit with one bottle containing daunorubicin base and a second bottle containing an organic liquid comprising alcohol, ethanol, benzyl alcohol, PEG, oleic acid, a median chain triglyceride, polysorbate, etc., or mixtures thereof. The kit is designed for mixing before administration into a malignant mass including a cancer or sarcoma. As the product formed after mixing the two bottles of the kit will be injected immediately, it does not matter whether the drug formed is the solution, suspension, emulsion or mixtures thereof.

Doxorubicin base has a molecular formula of $C_{27}H_{29}NO_{11}$. Its molecular weight is 543.5 g/mol. It is slightly soluble alcohols; moderately soluble in anhydrous methanol. The pH of 10 mg of doxorubicin base in 5 ml of water, is 7.9. There currently are no formulations of doxorubicin base on the market.

The doxorubicin intratumor injectable formulation of the present invention can be a solution, a water in oil type nano emulsion, or a suspension. The method of production of the doxorubicin base injection can be in the form of a solution, a suspension or a water in oil emulsion similar to that of daunorubicin basic intratumor injection. The nano emulsion comprises doxorubicin base (e.g. from about 0.2% to about 1.5%) dissolved in the organic solvent by volume (e.g. from about 85% to about 96%). The preferred embodiment comprises from about 40 to about 85% of oleic acid, from about 60% to about 15% of an alcohol such as ethanol, benzyl alcohol, or mixtures thereof, from about 4 to about 15% of water and from about 0.1% to about 1% of acetic acid as buffer. It is not stable when stored at room temperature for two months, but is stable when stored below −5° C. for two months. The invention can be manufactured, e.g., by reacting from about 0.2% to about 1.5% of a doxorubicin hydrochloride and the same molar weight of sodium hydroxide in about 5% of water for injection of the v/v of the injection in a container. The desalination base can be e.g., sodium carbonate, bicarbonate, sodium acetate, sodium phosphate, bi-sodium phosphate, potassium carbonate, potassium bicarbonate, potassium acetate or potassium phosphate or mixtures thereof. to form doxorubicin base. Then e.g. from about 85% to about 96% of an organic liquid such as ethanol and e.g. from about 40% to about 85% of oleic acid is added into the container, which is added with e.g. from about 0.1% to about 0.5% of acetic acid as the buffer.

The epirubicin intratumor injectable formulation of the invention is an organic solution, suspension or a water in oil type nano emulsion. The nano emulsion comprising e.g., from about 0.2% to about 1.5% of epirubicin base dissolved in e.g. from about 85% to about 96% of the organic solvent by volume. The preferred embodiment comprises from about 30 to about 85% of oleic acid, from about 70 to about 15% of an alcohol such as ethanol, benzyl alcohol, or mixtures thereof, from about 4% to about 15% of water, and from about 0.1% to about 1% of acetic acid as buffer. The formulation is not stable when stored at room temperature for e.g. two months, but is stable when stored below −5° C. for eight months.

The water in oil type nano emulsion of the epirubicin base formulation of the present invention was manufactured by reacting an epirubicin hydrochloride and the same molar weight of sodium hydroxide in about 4% to about 15% of water for injection of the v/v of the injection in a container. The base for desalination can be sodium carbonate, bicarbonate, sodium acetate, sodium phosphate, bi-sodium phosphate, potassium carbonate, potassium bicarbonate, potassium acetate, potassium phosphate, etc. In a preferred embodiment, from about 0.3% to about 1.5% of epirubicin hydrochloride and the same molar weight of sodium hydroxide was put in from about 4% to about 10% of water of the v/v of the injection in the container. Then from about 90% to about 96% of an organic liquid, such as ethanol and oleic acid was added into the container, which was added with from about 0.1% to about 1% of of acetic acid as the buffer. The solution of the invention was then passed through a 0.22 micron filter after which approximately 4.2 ml of filtrate is filled into a vial under nitrogen.

Epirubicin base is free from hydrochloride. The formula of the epirubicin base of the present invention is $C_{27}H_{29}NO_{11}$ and its molecular weight is 543.5 g/mol. The epirubicin base is a deep brown powder and is insoluble in water. The solubility of epirubicin base in water is 0.093 mg per ml. The pH of epirubicin base in water is pH 8.0. Currently, there is no epirubicin base formulation in the market.

The epirubicin intratumor injectable solution or suspension of the invention was manufactured by direct mixing epirubicin base (e.g. from about 0.2% to about 1.5%) with an organic solvent, solution or a mixture thereof (e.g. from about 98.5% to about 99.8%). The organic liquid comprises an alcohol such as ethanol or benzyl alcohol, PEG, oleic acid, a median chain triglyceride, polysorbate, etc., or mixtures thereof.

The mitoxantrone contained in the present invention is a mitoxantrone base which does not have hydrochloride. The formula of mitoxantrone base is $C_{22}H_{28}N_4O_6$ and its molecular weight is 444.5 g/mol. Mitoxantrone base is sparingly soluble in water; slightly soluble in methanol; practically insoluble in acetonitrile chloroform and acetone. The pH of mitoxantrone base in water is pH 9.42. (25 mg/in 10 ml water).

The mitoxantrone intratumor injectable formulation of the invention is an organic solution, suspension or a water in oil type nano emulsion. The nano emulsion comprises a mitoxantrone base (e.g. from about 0.05% to about 0.2%) dissolved in an organic solvent by volume (e.g. about 99.5%). The preferred embodiment comprises from about 30% to about 85% of oleic acid, from about 70% to about 15% of an alcohol, such as ethanol, benzyl alcohol, or mixtures thereof, from about 1% to about 5% of water, and from about 0.1% to about 1% of acetic acid as buffer. It is not stable when stored at room temperature for two months, but is stable when stored below −5° C. for e.g. three months.

The water in oil type nano emulsion of the mitoxantrone base formulation of the present invention is manufactured by reacting mitoxantrone hydrochloride (e.g. from about 0.05% to about 0.2%) with the same molar volume of sodium hydroxide in water for injection of the v/v of the injection in a container (e.g. from about 4% to about 10%). The base for desalination can be sodium carbonate, bicarbonate, sodium acetate, sodium phosphate, bi-sodium phosphate, potassium carbonate, potassium bicarbonate, potassium acetate, potassium phosphate, etc. Then an organic liquid, such as ethanol and oleic acid (e.g. from about 90% to about 96%), is added into the container, which is added with acetic acid as the buffer (e.g. 0.1% to about 0.5%). The solution of the invention was passed through a 0.22 micron filter and then 4.2 ml of filtrate is filled into a vial under nitrogen.

The mitoxantrone intratumor injectable solution or suspension of the present invention is manufactured by direct mixing of mitoxantrone base with the suitable amount of organic solvent, solution or the mixture. The organic liquid comprises an alcohol such as ethanol, benzyl alcohol, PEG, oleic acid, a median chain triglyceride, polysorbate, etc., or mixtures thereof.

The base form of vinca alkaloids differs from the sulfate salt form. A comparison of the base form of vinca alkaloids with the sulfate form is shown in the Table 2.

TABLE 2

Comparison of base form versus sulfate salt form of vinca alkaloids

|  | Vinblastine | Vinblastine $H_2SO_4$ | Vincristine | Vincristine $H_2SO_4$ | Vindesine | Vindesine $H_2SO_4$ |
|---|---|---|---|---|---|---|
| MW (g/mol) | 811 | 909.1 | 825 | 923 | 753.9 | 852 |
| Solubility in $H_2O$ | no | yes | no | yes | no | yes |
| Solubility in oil | yes | no | yes | no | yes | no |
| Solubility in ethanol | yes | no | yes | no | yes | no |

The vinblastine intratumor injection of the present invention may be an organic solution, suspension or a nano water in oil type emulsion. The vinblastine intratumor injection solution was produced by the addition of vinblastine base into an organic liquid such as an alcohol, a median chain triglyceride, glycerol, vegetable oil, oleic acid, PEG or mixture of any of the above.

The vinblastine intratumor nano water in oil emulsion injection of the present invention is manufactured by reaction of vinblastine sulfate (e.g. 0.1% to about 1%) with about the same molar weight of a basic solution, such as NAOH, sodium acetate, sodium carbonate, disodium phosphate, and sodium phosphate, sodium citrate, potassium salt, potassium hydroxide, potassium acetate etc. The resulting vinblastine base is mixed with e.g. from about 95% to about 99% of a mixture of ethanol (e.g. 20% to about 70%) with a median chain triglyceride, glycerol, vegetable oil, oleic acid, PEG or a mixture of any of the above (e.g. 30% to about 80%). Then a small amount of acetic acid is added as the buffer (e.g. 0.1% to about 0.5%). The solution of the invention was passed through a 0.22 micron filter and then 4.2 ml of filtrate is filled into a vial under nitrogen.

Vinblastine sulfate is soluble in water, but vinblastine base is not soluble in water. The molecular formula of vinblastine base is $C_{46}H_{58}N_4O_9$ and the molecular weight is 811 g/mol. It is a light green to white powder. Vinblastine is practically insoluble in water, but soluble in alcohol, acetone, chloroform, ethyl acetate and is unstable at room temperature.

Vinblastine sulfate injections contain more than 95% of water by volume, but the water content of vinblastine base injection contains no more than 10% by volume of the injection. The water content of vinblastine base injection may be as low as less than 3% of the volume of the injection.

Vincristine base is not soluble in water. The vincristine intratumor injection may be an organic solution, suspension or a nano water in oil type emulsion. The method of production of vincristine intratumor injection is similar to that of vinblastine intra tumor injection. The solvent of the solution may comprise different organic liquids such as a median chain triglyceride, glycerol, vegetable oil, oleic acid, ethanol or a mixture of any of the above. For a vincristine base injection solution or suspension, the formulation contains no more than 1% of water by volume of the injection. The vincristine intratumor injection solution of the present invention is produced by the addition of from about 0.5% to about 1% of vincristine base into a mixture of from about 15% to about 70% of alcohol with from about 30% to about 85% of an organic liquid such as a median chain triglyceride, glycerol, vegetable oil, oleic acid, or mixture of any of the above.

A vincristine intratumor injection nano water in oil emulsion is produced by the reaction of vincristine sulfate (e.g. 0.05% to about 0.5%) with about the same molar weight of a base in from about 1% to about 10% of aqueous solution, after which a mixture of about 90% to about 99% of organic solvent was added, the organic solvent containing an alcohol with from about 15% to about 70% of the volume of the emulsion, from about 30% to about 85% of a different organic liquid such as median chain triglyceride, glycerol, oleic acid, vegetable oil, or mixture of any of the above, is added into the resultant mixture of the above reaction. The alcohol can comprise e.g. ethanol, benzyl alcohol and is used to reduce the viscosity of the injection. The nano emulsion contains from about 1.5 to about 10% of water by volume, from about 0.1% to about 0.5% of acetic as the buffer. The amount of water should not be too high otherwise the emulsion will break into two layers. The pH of the emulsion was about 4.-6.05. Vincristine intratumor injection nano water in oil emulsion contains ethanol and oleic acid and the average particle size was 15.3 nm. For vincristine intratumor injection emulsion containing the ethanol and glycerol, the average particle size was 115.2 nm. This may be due to the high viscosity of the glycerol which might not have been homogenized to make the particle smaller.

Vindesine base is amorphous solid, its mp>250° C. The molecular formula of vindesine base is $C_{43}H_{55}N_5O_7$ and its molecular weight is 753.93. It is a powder at room temperature and is practically insoluble in water. It is soluble in alcohol, acetone. There is not any vindesine base injection on the market.

The vindesine intratumor injection may be an organic solution, suspension or a nano water in oil type emulsion. The vindesine intratumor injection solution or suspension is produced by the addition of vindesine base into a mixture of alcohol with a different organic liquid such as median chain triglyceride, glycerol, vegetable oil, oleic acid, or mixture of any of the above. But the vindesine base is not stable it is not easy to commercialize the base chemicals.

Vindesine intratumor injection nano W/O type emulsion is produced by the desalination of from about 0.05% to about 1% of vindesine sulfate with about the same molar weight of sodium hydroxide aqueous solution, then a mixture of from about 15% to about 70% of alcohol with a different organic liquid such as a median chain triglyceride, glycerol, vegetable oil, oleic acid, or mixture of any of the above in an amount of from about 30% to about 70% is added into the resulting vindesine base mixture produced during desalination. The resulting vindesine base injection contains no more than 5% of water by volume of the injection and it is an oily solution. The nano emulsion contains from about 1.0% to about 5% of water by volume, from about 0.1% to about 1% of acetic acid as the buffer. The amount of water should not be too high otherwise the emulsion will break into two layers. The pH of the emulsion was about 4.-6.05.

Mechlorethamine base intratumor injection may be an organic solution, suspension or a nano water in oil type emulsion. The mechlorethamine intratumor injection solution is produced by the addition of from about 0.1% to about 1% of mechlorethamine base into a mixture of from about 15% to about 70% of an alcohol with a different organic liquid such as a median chain triglyceride, glycerol, vegetable oil, oleic acid, or mixture of any of the above. The proportion of the organic solvent beside alcohol is about 30% to 85% of the volume of the emulsion The mechlorethamine base is produced by reaction of from about 0.1% to about 1% of mechlorethamine hydrochloride with an equal molar weight of sodium hydroxide aqueous solution in a large beaker, then from about 1 to 10 times of the weight of the mechlorethamine base of trichloromethane is added into the beaker, the contents of which was transferred into a separating funnel. The mechlorethamine trichloromethane solution is transferred to a rotary evaporator, then the trichloromethane is evaporated out of the evaporator. The residual liquid is the mechlorethamine base. The mechlorethamine base is a colorless liquid which is very irritating and dangerous. It will dissolve a plastic glove if it comes in contact with it. The manufacturing, storage and handling of this chemotherapeutic base is very dangerous and involves many complicated procedures. Therefore, it is preferable to manufacture the intratumor injection in a simple way to prevent industrial accidents. The manufacturing of intratumor injection in a nano emulsion is a safe, convenient and simple process.

Mechlorethamine intratumor injection nano water in oil type emulsion is produced by the desalination of from about 0.1% to about 1% of mechlorethamine hydrochloride with the same molar weight of sodium hydroxide aqueous solution or another chemical base such as sodium carbonate, bicarbonate, sodium acetate, sodium phosphate, bi-sodium phosphate, and etc. Then a mixture of organic liquid from about 95% to about 99% of the volume of the emulsion was added into the above solution, which contains from about 15% to about 70% of an alcohol with from about 30% to about 85% of a different organic liquid such as a median chain triglyceride, glycerol, vegetable oil, oleic acid, or a mixture of any of the above, is added into the resultant mechlorethamine base mixture produced during desalination. Mechlorethamine base injection contains no more than 10% of water by volume of the injection and it is an oily solution. The nano emulsion contains from about 0.1% to about 3% of acetic acid as the buffer. The amount of water should not be too high otherwise the emulsion will break into two layers. The pH of the emulsion was about 4.-6.05. The solution of the invention is passed through a 0.22 micron filter and then 2.2 ml of filtrate is filled into a vial under nitrogen.

Bendamustine base has a molecular formula of $C_{16}H_{21}Cl_2N_3O_2$ and its molecular weight is 358.3 g/mol. Bendamustine is a bifunctional mechlorethamine derivative with alkylating and antimetabolite activities. There is no bendamustine base injection in the market for intratumor injection.

Bendamustine base intratumor injection may be an organic solution, suspension or a nano water in oil type emulsion. Bendamustine intratumor injection solution or suspension is produced by the addition of from about 1% to about 4% of bendamustine base into a mixture of from about 15% to about 65% of an alcohol with from about 30% to about 80% of a different organic liquid, such as a median chain triglyceride, glycerol, oleic acid, PEG or mixture of any of the above.

Bendamustine intratumor injection nano water in oil emulsion is produced by the desalination of from about 1% to about 4% of bendamustine hydrochloride with about the same molar weight of sodium hydroxide aqueous solution, then a mixture of from about 15% to about 65% of an alcohol with a different organic liquid such as PEG, median chain triglyceride, glycerol, vegetable oil, oleic acid, or mixture of any of the above, in an amount of from about 30% to about 80% of, was added into the bendamustine base mixture produced during desalination. Bendamustine base injection contains no more than 10% of water by volume of the injection and it is a nano emulsion. The nano emulsion contains from about 0.5% to about 2% of acetic acid as the buffer. The amount of water should not be too high otherwise the emulsion will break into two layers. The pH of the emulsion was from about 4 to about 6.05. The solution of the invention is passed through a 0.22 micron filter and then 2.2 ml of filtrate is filled into a vial under nitrogen.

Eribulin intratumor injection nano water in oil type emulsion is produced by the desalination of from about 0.05% to about 1% of eribulin mesylate with about the same molar weight of sodium hydroxide aqueous solution. Then a mixture of from about 15% to about 70% of alcohol with a different organic liquid such as a median chain triglyceride, glycerol, vegetable oil, oleic acid, or a mixture of any of the above in an amount of from about 30% to about 70% is added into the resulting eribulin base mixture produced during desalination. The resulting eribulin base injection contains no more than 5% of water by volume of the injection and it is an oily solution. The nano emulsion contains from about 1.0% to about 5% of water by volume, from about 0.1% to about 1% of acetic acid as the buffer. The amount of water should not be too high otherwise the emulsion will break into two layers. The pH of the emulsion was about 4.-6.05.

The invention may be a solution without water and is prepared by the dissolving of a basic chemotherapeutic drug into an organic liquid such as daunorubicin base, epirubicin base, amrubicin base, doxorubicin base or mitoxantrone base in a mixture of ethanol and oleic acid. In other embodiments of the invention, the solution may be a vinblastine base, vincristine base or a vindesine base dissolved in a mixture of ethanol with a median chain triglyceride, glycerol, oleic and/or PEG of a molecular weight of 200 to 400. In another embodiment of the invention, the solution may be an alkylating base including mechlorethamine base, bendamustine base, chlorambucil, ifosfamide, cyclophosphamide, melphalan, carmustine, lomustine, streptozocin, busulfan, dacarbazine, temozolomide, altretamine and thiotepa dissolved in a mixture of ethanol with median chain triglyceride, glycerol, oleic and/or PEG of molecular weight of 200 to 400.

If the solubility of the chemotherapeutic base in the organic liquid is low and the injection of the invention contains a higher concentration of a base such as mitoxantrone base, the solution is over saturated and becomes an injectable suspension. In such cases, there is a problem of sterilization because most chemotherapeutic bases cannot tolerate terminal heat sterilization. The suspension can be produced by the addition of preservative. However, the quality of a suspension that contains a preservative is poorer than that of a solution made by filtration because the basic active drug ingredient is not evenly distributed in the liquid and the particle size is different. In addition, the invention may contain bacteria and the endotoxin may be higher than the solution contained. Another way to produce the basic chemotherapeutic intratumor injection of the present invention was carried out by directly reacting the acidic salt of the chemotherapeutic drug with a basic solution such as sodium hydroxide. For example, when producing a mitoxantrone base injection, the following method was used: 236 mg of mitoxantrone hydrochloride was added into a beaker of 6 ml of water, and then 1 ml of water with 36.7 mg of sodium hydroxide was added into the above solution of mitoxantrone HCL. 100 ml of glycerol, 85 ml of ethanol and a small amount of acetic acid was added into the beaker. The pH tested was 6.48, then 0.35 ml of acetic acid was added into the beaker, the pH tested was 4.57. An additional amount of ethanol was added into the beaker until the volume reached 200 ml. The solution formed was filtered and the filtration was filled into a vial and stoppered. The invention formed in the above procedure consisted of less than 6% of water, a small amount of sodium chloride, glycerol and ethanol. The amount of sodium chloride comes from mitoxantrone HCL and is the same molar amount as the acidic salt. The particle size of the mixture tested was about 50 nm. The mixture of the invention is a blue clear water in oil nano emulsion.

The base form of chemotherapeutic agents is difficult to produce and is unstable. The shelf life of the base of the intermediate of the injection is short. In order to overcome these problems, certain embodiments of the present invention include the basic chemotherapeutic drug in the injection formulation of the present invention made by desalination of the acidic salt of chemotherapeutic drug in a column of octadecyl silane chemically bonded silica (ODS). The base formed in the ODS is washed out and mixed in a mixture of alcohol with a suitable organic liquid such as a median chain triglyceride, glycerol, oleic acid, polysorbate and PEG of molecular weight of 200 to 400. This basic solution is free of water and sodium chloride or sodium sulfate. The basic chemotherapeutic drug has low solubility in organic liquids, even in the presence of an organic acid. If the solution of the invention has a low concentration of active basic drug, it will not be potent enough to kill cancer cells because the diffusion of the drug through the cell membrane is proportional to the concentration of the drug outside the cell membrane.

DETAILED DESCRIPTION OF THE PREFERRED EMBODIMENTS

The following examples of anticancer formulations in accordance with the present invention are not to be construed as limiting the present invention in any manner and are only examples of the various formulations described herein. It is contemplated that injectable formulations of the invention as described below can be prepared at about the time the patient is to be treated, for example, one vial may contain the basic chemotherapeutic drug, e.g. an anthracycline base such as doxorubixin base, a vinca alkaloid base or a basic alkylizing agent and another vial may contain the solvent and any other optional pharmaceutical excipients suitable for injection, and these materials may then be mixed prior to direct injection into a tumor in the patient as described herein. Alternatively, it is also contemplated that the method of manufacture described herein may be used to prepare a premixed injectable formulation (preferably stable as defined herein) and that this injectable formulation is then stored in a pharmaceutically acceptable container(s) (e.g., vial) under acceptable storage conditions for later use. Scale-up of the methods of manufacture set forth below are also contemplated.

The chemotherapeutic base comprising a vinca alkaloid base, an alkylating agent base, an anthracycline base or eribulin base, may be purchased by an appropriate manufacturer or can be produced in a laboratory through the desalination of the vinca alkaloid sulfate, eribulin mesylate, anthracycline hydrochloride or alkylating agent (e.g., bendamustine hydrochloride). The injectable basic chemotherapeutic formulation of the present invention may be made by adding together a chemotherapeutic base with an appropriate organic liquid. The manufactured product will be a solution or suspension if the concentration of the basic chemotherapeutic drug is too high.

Example 1: Daunorubicin Base Formulation Comprising Ethanol and $PEG_{300}$ 200 ml of $PEG_{300}$ was poured into a beaker which was heated to 40° C. in a water bath. Then 2.070 gram of daunorubicin base was added into the beaker with stirring (the contents of the beaker was under shearing conditions). An amount of about 200 ml of dehydrated ethanol was added into the beaker until the volume of the contents of the beaker reached 400 ml. The resultant solution was passed through a 0.22-micron filter while applying nitrogen, then 4.2 ml of filtrate was filled into a vial and a stopper was inserted in the vial and then the vial was sealed with an aluminum cap. The solution was red.

Example 2: Daunorubicin Base Formulation Comprising $PEG_{300}$ 400 ml of $PEG_{300}$ was poured into a beaker which was heated in a water bath at 41° C. Then 2.068 g of daunorubicin base was added into the beaker with mixing and the contents of the beaker were vibrated by ultrasound vibration for 1 hour. The resultant solution was passed through a 0.22-micron filter while applying nitrogen, then 5.05 ml of filtrate was filled into a vial and a stopper was inserted in the vial and then the vial was sealed with an aluminum cap. The solution was deep red.

Example 3: Daunorubicin Base Formulation with 70% $PEG_{400}$ & 30% Ethanol 560 ml of $PEG_{400}$ was poured into a beaker which was heated in a water bath at 30° C. Then 2.743 g of daunorubicin base was added into the beaker with mixing after which 220 ml of dehydrated ethanol was added into the beaker. The contents of the beaker were vibrated by ultrasound vibration for 5 minutes. An additional amount of about 20 ml of dehydrated ethanol was added into the beaker until the volume of the contents of the beaker reached a total volume of 800 ml. The resultant solution was passed through a 0.22-micron filter while applying nitrogen, then 5.3 ml of filtrate was filled into a vial. A stopper was inserted in the vial and then the vial was sealed with an aluminum cap.

Example 4: Daunorubicin Base Formulation with 70% Oleic Acid and 30% Alcohol 350 ml of oleic acid was poured into a beaker which was heated in a water bath at 30° C. Then 1.757 g of daunorubicin base was added into the beaker with mixing and then 130 ml of dehydrated ethanol was added into the beaker. The contents of the beaker were vibrated by ultrasound vibration for 10 minutes. An additional amount of dehydrated ethanol was added into the beaker until the volume of the contents of the beaker reached 500 ml. The resultant solution was passed through a 0.22-micron filter while applying nitrogen, then 5.3 ml of filtrate was filled into a vial. A stopper was inserted in the vial and then the vial was sealed with an aluminum cap. The solution was deep red.

Example 5: Daunorubicin Base W/O Emulsion Containing 40% Oleic Acid and Alcohol 5 ml of injection water and 4534 mg of daunorubicin hydrochloride was added into a beaker (B) of 400 ml size, the content was stirred until the daunorubicin HCL was dissolved. 2972 mg of sodium hydroxide and 10 ml of water for injection was poured into another beaker (A) of 20 ml size. 1 ml of solution of beaker A was added into beaker B, which was stirred evenly. 82.8 g of dehydrated ethanol was added into beaker B, the contents of which were stirred too. A small amount of acetic acid/ethanol (ratio ¼) solution was added into beaker B, until the solution was clear. 71.1 g (80 ml) of oleic acid was added into beaker B, which was stirred. An additional amount of ethanol was added into the beaker until the weight of the contents of beaker B reached 171 grams (200 ml). The solution formed was then passed through a filter of 0.22 um size. 2.2 ml of filtrate was filled into a vial. A stopper was inserted into the vial and the vial was sealed with an aluminum cap under nitrogen. The solution after filtration was red clear and transparent.

A number of other formulas of daunorubicin solution was made as in the following tables. It was found that the related matter was related to the pH of the solution, the range of pH of the injection is from about 4 to about 6, the preferred pH is from about 4.5 to about 6.

Example 6: Mitoxantrone Base Formulation Comprising Oleic Acid and Ethanol 250 ml of oleic acid and 180 ml of dehydrated ethanol was poured into a beaker which was heated by a water bath to 30° C., then 507 mg of mitoxantrone base was added into the beaker with mixing. The contents of the beaker were vibrated by ultrasound for 10 minutes. The solution was deep blue. An additional amount of dehydrated ethanol was added into the beaker until the volume of the contents of the beaker reached 500 ml. The resultant solution was passed through a 0.22-micron filter while applying nitrogen, then 5.2 ml of filtrate was filled into a vial. A stopper was inserted in the vial and then the vial was sealed with an aluminum cap. The solution was blue.

Example 7: Mitoxantrone Base Formulation Comprising Oleic Acid with Acetic Acid 490 ml of oleic acid and 10 ml of acetic acid was poured into a beaker, then 508 mg of mitoxantrone base was added into the beaker which was heated to 30° C. The contents of the beaker were vibrated by ultrasound vibration for 20 minutes. The resultant solution was passed through a 0.22-micron filter while applying nitrogen, then 5.2 ml of filtrate

TABLE 3

Summary of Daunorubicin Injection tested results

| Batch No. | PH 3-6 | Assay 90-115% | Daunorubicinone (≤1.0%) | Doxorubicin (≤1.0%) | Daunorubicinol (≤1.5%) | Any other Impurity ≤1.0% | Total of other impurities (≤2.5%) | Total impurity | Cl % | H2O % (v/v) |
|---|---|---|---|---|---|---|---|---|---|---|
| 1030 2 ml:40 mg | 5.808 | 103.2% | 0.20% | 0.07% | 0.03% | 0.09% | 0.35% | 0.65% | 6.99% | 6.12% |
| 1124 2 ml:40 mg | 5.228 | 100.9% | 0.21% | 0.16% | 0.03% | 0.24% | 1.03% | 1.43% | 3.57% | 4.34% |
| 1125 2 ml:40 mg | 4.482 | 101.3% | 0.18% | 0.18% | 0.04% | 0.09% | 0.36% | 0.76% | 5.52% | N/A |
| 1202 2 ml:40 mg | 4.660 | 83.9% | 0.17% | 0.23% | 0.04% | 0.30% | 0.86% | 1.30% | 5.38% | N/A |
| 1203 2 ml:40 mg | 4.83 | 100.7% | 0.21% | 0.25% | 0.03% | 0.12% | 0.38% | 0.87% | 6.99% | 5.81% |
| 1204 2 ml:30 mg | 4.484 | 100.9% | 0.21% | 0.19% | 0.03% | 0.09% | 0.48% | 0.91% | 5.09% | 4.12% |
| 1208 2 ml:30 mg | 4.495 | 101.7% | 0.20% | 0.21% | 0.04% | 0.09% | 0.52% | 0.97% | 6.89% | 5.12% |

The preferred range of oleic acid is from about 35 to about 70% and the range of ethanol is from about 25% to about 60% and the amount of water is less than 6.5% (v/v) of the injection. As the $LD_{50}$ of the oleic acid is low, a concentration of less than 50% of oleic acid is preferable. If the contents of the ethanol are too high, the injection will not become solid below 0° C.; if the injection is in liquid state, the invention is not stable. Therefore, the preferred content of ethanol was from about 25% to about 60% of the volume of injection.

The invention above is a water in oil nano emulsion. The water content is from about 4% to about 7% v/v of the injection and the diameter of the microsphere of the daunorubicin base injection tested by PPS is about 51-54.3 nanometer. The nano emulsion contains aqueous sodium chloride solution.

It is Applicant's position that FIG. 1, which shows an intensity-weighted NICOMP distribution analysis, evidences that the formulation is an emulsion as would be understood by one of skill in the art.

was filled into a vial. A stopper was inserted in the vial and then the vial was sealed with an aluminum cap. The resultant solution was blue.

Example 8: Mitoxantrone Base Formulation Comprising PEG with Acetic Acid 450 ml of $PEG_{300}$ was poured into a beaker, then 508 mg of mitoxantrone base was added into the beaker which was heated to 30.9° C. The contents of the beaker were vibrated by ultrasound vibration for 20 minutes. Then 5 ml of acetic acid was added into the beaker. An additional amount of $PEG_{300}$ was added into the beaker until the volume of the contents of the beaker reached 500 ml. The resultant solution was passed through a 0.22-micron filter while applying nitrogen, then 5.2 ml of filtrate was filled into a vial. A stopper was inserted in the vial and then the vial was sealed with an aluminum cap. The resultant solution was blue.

Example 9: Mitoxantrone Base Formulation Comprising PEG and Ethanol 450 ml of dehydrated ethanol and 500 ml of $PEG_{300}$ was poured into a beaker which was heated to 40° C., and then 1.004 gram of mitoxantrone base was added into the beaker with mixing (the contents of the beaker under shearing conditions). An additional amount of ethanol was added into the beaker until the volume of the contents of the beaker reached 1000 ml. The resultant solution was passed through a 0.22-micron filter while applying nitrogen, then 5.3 ml of filtrate was filled into a vial. A stopper was inserted into the vial and then the vial was sealed with an aluminum cap. The solution was deep blue.

Example 10: Mitoxantrone Base Formulation Made by Reaction of Mitoxantrone HCL with NAOH 471 mg of mitoxantrone hydrochloride and 9 ml of water for injection was added into a 400 ml beaker (beaker A), the contents of which were stirred. The solution is dark blue. 10 ml water for injection and 734 mg of sodium hydroxide was added into a 20 ml beaker (beaker B), it then it was stirred. 1 ml of sodium hydroxide solution from a beaker B and 5 ml of anhydrous ethanol was transferred to beaker A, and then the contents of beaker A were stirred.

Then 100 ml of dehydrated ethanol was added into beaker A, and it was stirred at 22° C. A small amount of acetic acid was added into beaker A until the solution was clear. 80 ml of oleic acid was added into the beaker A. An additional amount of ethanol was added into the beaker A until the volume of the contents of beaker A reached 200 ml. The resultant solution was passed through a 0.22 micron filter while applying nitrogen, then 5.2 ml of filtrate was filled into a vial. A stopper was inserted into the vial and then the vial was sealed with an aluminum cap under nitrogen. The solution was blue, chloride tested was 13.3%, the pH tested was 3.75. The particle size tested: 72.5% was 2.2 nm, 27.5% was 181.4 nm. The total of other impurities was 0.69%.

Example 11: Mitoxantrone Emulsion Made by Reaction of Mitoxantrone HCL with NAOH Comprising 50% Glycerol/Ethanol/1 mg/ml 236 mg of mitoxantrone hydrochloride and 5.943 ml of water for injection was added into a 400 ml beaker (beaker A), the contents of which was stirred. The solution is dark blue. 10 ml water for injection and 367 mg sodium hydroxide was added into a 20 ml beaker (beaker B) and then stirred. 1 ml of sodium hydroxide solution from beaker B and 5 ml of anhydrous ethanol was transferred to beaker A, and then the contents of beaker A were stirred. Then 100 ml of glycerin and 3 drops (45 mg) of acetic acid was added into beaker A, and the contents stirred at 22° C. 85 ml of dehydrated ethanol was added into beaker A.

The pH tested was 6.478, then 0.35 ml of acetic acid was added into beaker A, and the pH measured was 4.574. An additional amount of ethanol was added into beaker A until the volume of the contents of beaker A reached 200 ml. The resultant solution was passed through a 0.22-micron filter while applying nitrogen, then 5.2 ml of filtrate was filled into a vial. A stopper was inserted into the vial and then the vial was sealed with an aluminum cap under nitrogen. The solution was blue, the chloride tested was 12.6.3%, the pH tested was 4.166. The particle size tested: 68.7% was 39.3 nm, 31.3% was 179.9 nm. The total of other impurities was 0.99%.

Example 12: Epirubicin Base Formulation Comprising Oleic Acid and Ethanol 250 ml of oleic acid and 230 ml of dehydrated ethanol was poured into a beaker which was heated in a water bath at 30° C. 1200 mg of epirubicin base was then added into the beaker with stirring. The contents of the beaker were vibrated by ultrasound vibration for 10 minutes. An additional amount of dehydrated ethanol was added into the beaker until the volume of the contents of the beaker reached 500 ml. The solution was passed through a 0.22 micron filter and then 5.2 ml of filtrate was filled into a vial under nitrogen. The solution was red.

Example 13: Epirubicin Base Formulation with PEG and Ethanol 560 ml of $PEG_{300}$ was poured into a beaker which was heated in a water bath at 30° C., then 1999 mg of epirubicin base was added into the beaker with stirring. 230 ml of dehydrated ethanol was added into the beaker and the contents of the beaker were vibrated by ultrasound vibration for 10 minutes. An additional amount of dehydrated ethanol was added into the beaker until the volume of the contents of the beaker reached 800 ml. The solution was passed through a 0.22 micron filter and then 5.3 ml of filtrate was filled into a vial under nitrogen. The solution was red.

Example 14: Epirubicin Base Formulation Comprising 40% Oleic Acid/Ethanol 4 mg/ml 447 mg of epirubicin hydrochloride and 4.5 ml of water for injection was added into a 200 ml beaker (beaker A), the contents of which were stirred. Beaker A was then placed in an ice water bath. 5 ml of water for injection and 617 mg of sodium acetate were added into a 20 ml beaker (beaker B) and then stirred. 0.5 ml of sodium acetate solution from beaker B and 10 ml of dehydrated ethanol was transferred to beaker A and then stirred. 40 ml of dehydrated ethanol and 40 ml of oleic acid was added into beaker A. The pH tested was 4.74. An additional amount of ethanol was added to beaker A until the volume of the contents of beaker B reached 100 ml. The resultant solution was passed through a 0.22-micron filter while applying nitrogen, then 2.2 ml of filtrate was filled into a vial. A stopper was inserted into the vial and the vial was sealed with an aluminum cap under nitrogen. The assay was 97, the pH was 5.07, the water content was 5.65% and the total related matter was 2.47%. The particle size was 37.4 nm.

Example 15: Doxorubicin Base Formulation Comprising PEG and Ethanol 280 ml of $PEG_{300}$ was poured into a beaker which was heated in a water bath at 30° C., then 1001 mg of doxorubicin base was added into the beaker with stirring. 100 ml of dehydrated ethanol was added into the beaker and the contents of the beaker were under ultrasound vibration for 10 minutes. An additional amount of dehydrated ethanol was added into the beaker until the volume of the contents of beaker B reached 400 ml. The solution was passed through a 0.22 micron filter and then 5.3 ml of filtrate was filled into a vial under nitrogen. The solution was red.

Example 16: Doxorubicin Base Formulation Comprising Oleic Acid and Ethanol 250 ml of oleic acid and 230 ml of dehydrated ethanol was poured into a beaker which was heated in a water bath at 30°

C., then 1201 mg of doxorubicin base was added into the beaker with stirring. The contents of the beaker were vibrated by ultrasound vibration for 10 minutes. An additional amount of dehydrated ethanol was added into the beaker until the volume of the contents of the beaker reached 500 ml. The solution was passed through a 0.22 micron filter and then 5.2 ml of filtrate was filled into a vial under nitrogen. The solution was red.

Example 17: Doxorubicin Base Formulation Comprising 40% Oleic Acid and Ethanol 18.2 g of octadecyl silane chemically bonded silica (ODS) was put into a beaker. 54 ml of dehydrated ethanol was added into the beaker and the contents of the beaker were mixed well, and then the ODS solution was filled into a glass chromatographic column (15 mm*400 mm). 767 mg of doxorubicin hydrochloride and 115 ml of water for injection was added into a beaker and then stirred for 45 minutes to dissolve the doxorubicin hydrochloride.

The doxorubicin hydrochloride solution was slowly poured into the glass chromatography column. 78 mg of sodium hydroxide was mixed with 300 ml of water, after which it was poured into the chromatographic column too.

66 ml of dehydrated ethanol, 60 ml (53.08 g) of oleic acid, and 0.2 ml of acetic acid were added into a beaker, the contents of which were mixed well. The mixture in the beaker was poured into the chromatographic column and, after 5 minutes, the piston was opened, the solution was poured out, and then 20 ml of dehydrated ethanol was added into the column. The solution of the column was collected by a beaker (beaker A). The pH tested was 4.65. An additional amount of dehydrated ethanol was added into beaker A until the volume of the contents of beaker A reached 150 ml. The solution was passed through a 0.22 micron filter and then 4.2 ml of filtrate was filled into a vial under nitrogen. A stopper was inserted into the vial and then the vial was sealed with aluminum cap. The solution was red and clear.

Example 18: Vinblastine Base Formulation Comprising a Median Chain Triglyceride and Ethanol 504 mg of sodium hydroxide and 50 ml of water for injection was put in a 100 ml beaker (beaker A) and the contents were stirred. 56 mg of vinblastine sulfate was put in a 40 ml beaker (beaker B). 5 ml of solution from beaker A was transferred to beaker B, the contents of which were stirred to complete the reaction.

86.728 g (110 ml) of dehydrated ethanol and 80 ml of medium chain oil was added into beaker B and the contents were stirred. The pH of the contents was 7.11.

0.5 ml of acetic acid was added into beaker B, the pH was 3.6. A small amount of sodium hydroxide was then added into the beaker B and a final pH was 4.45. An additional amount of dehydrated ethanol was added into the beaker B, until the volume of the contents of beaker B reached 200 ml. The solution was passed through a 0.22 micron filter and then 2.2 ml of filtrate was filled into a vial under nitrogen. A stopper was inserted into the vial and then the vial was sealed with an aluminum cap. The injection of the solution was colorless, transparent and clear. The amount of water contained was 2.5%. The results of the two experiments of different formulas of vinblastine were as follows:

TABLE 4

Summary of Stability of Vinblastine Injection

Prescription
Vinblastine Injection, 40% medium-chain triglycerides + 60% ethanol
Strength
2 ml:5 mg, the particle size of W/O emulsion was 11.9 NM.

| Storage conditions | Time | PH | Assay | Maximum individual impurity(≤2.0%) | Total impurities ≤5.0% |
|---|---|---|---|---|---|
| / | 0-day | 4.556 | 109.1% | 0.55% | 1.41% |
| −20° C. | 24-days | 4.631 | 106.8% | 0.47% | 1.21% |
| −20° C. | 44-days | 4.608 | 105.9% | 0.46% | 1.23% |
| 2° C. | 24-days | 4.622 | 104.0% | 0.50% | 1.38% |
| 2° C. | 44-days | 4.587 | 106.3% | 0.45% | 1.58% |
| Conclusion | There is no obvious difference between −20° C. and 2° C. in content, but at 2° C., the related substances is higher. | | | | |

Prescription
Vinblastine Injection 70% medium-chain triglyceride + 30% ethanol
Strength
2 ml:5 mg, the particle size of W/O emulsion was 39.9 NM.

| Storage conditions | Time | PH | Assay (90.0%-110.0%) | Maximum individual impurity(≤2.0%) | Total impurities (≤5.0%) |
|---|---|---|---|---|---|
| / | 0-day | 4.269 | 102.8% | 0.49% | 1.47% |
| −20° C. | 10-days | 4.369 | 101.4% | 0.48% | 1.43% |
| −20° C. | 1-month | 4.283 | 102.9% | 0.46% | 1.43% |
| 2° C. | 10-days | 4.357 | 100.0% | 0.50% | 1.51% |
| 2° C. | 1-month | 4.265 | 101.9% | 0.52% | 1.79% |
| Conclusion | There is no obvious difference between −20° C. and 2° C. in content, at 2° C. the related substances is higher. | | | | |

The particle size is correlated to the content of ethanol in the injection; the more ethanol, the smaller the article size.

Example 19: Vinblastine Base Formulation Comprising Glycerol and Ethanol 453 mg of sodium hydroxide and 30.0 ml of water for injection was put in a 100 ml beaker (beaker A) and the contents were stirred. 540 mg of vinblastine sulfate was put in a 400 ml beaker (beaker B). 3 ml of the solution in beaker A and 5 ml of dehydrated ethanol was transferred to beaker B and the contents of Beaker B were stirred to make the reaction complete. 90 ml of dehydrated ethanol and 100 ml of glycerol were added into beaker B and the contents were stirred. The solution was clear. The pH of the contents of beaker B was 7.47. A small amount of acetic acid (approximately 6 drops) was added into beaker B. An additional amount of dehydrated ethanol was added into the beaker B, until the volume of the contents of beaker B reached 200 ml. The solution was passed through a 0.22 micron filter and then 2.2 ml of filtrate was filled into a vial under nitrogen. A stopper was inserted into the vial and the vial was then sealed with an aluminum cap. The injectable solution was colorless, transparent and clear. The pH was 5.17 and the content of water was 1.48%. The particle size was 39.9 nm.

Example 20: Vinblastine Base Formulation Comprising Oleic Acid and Ethanol 452 mg of sodium hydroxide and 30.0 ml of water for injection was put in a 100 ml beaker (beaker A) and the contents were stirred. 540 mg of vinblastine sulfate was put in a 400 ml beaker (beaker B). 3 ml of solution in beaker A and 5 ml of dehydrated ethanol was transferred to beaker B and the contents were stirred to complete the reaction. 100 ml of dehydrated ethanol and 80 ml of oleic acid were added into beaker B and the contents were again stirred. An additional amount of dehydrated ethanol was added to the beaker B until the volume of the contents of beaker B reached 200 ml. The solution of beaker B was passed through a 0.22 micron filter and then 2.2 ml of filtrate was filled into a vial under nitrogen. A stopper was inserted into the vial and then the vial was sealed with an aluminum cap. The injection of the solution was colorless, transparent and clear. The pH of the content was 4.95. The particle size was 89.6 nm.

Example 21: Vincristine Base Formulation Comprising 40% Oleic Acid and Ethanol 193 mg of sodium hydroxide and 20.0 g of water for injection was added into a 100 ml beaker (beaker A) and the contents were stirred. 246 mg of vincristine sulfate was added into a 400 ml beaker (beaker B). 2 ml of NaOH solution from beaker A and 3 ml of dehydrated ethanol was added into beaker B and the contents of beaker B were stirred. The resulting solution is turbid and milky white. 3 ml of dehydrated ethanol was added into beaker B. The appearance of the solution had no change. 71.1 g (80 ml) of oleic acid and 39.4 g (50 ml) of dehydrated ethanol were added into beaker B, after which the solution became clear and light yellow. The pH of the mixture was 4.26. A small amount of dehydrated ethanol was added into beaker B until the weight of the contents of beaker B were 166.453 g (200 ml). The solution was passed through a 0.22 micron filter and then 4.2 ml of filtrate was filled into a vial under nitrogen. A stopper was inserted into the vial and the vial was then sealed with an aluminum cap. The particle size of the water in oil emulsion was 15.3 nm.

Example 22: Vincristine Base Formulation Comprising 50% Glycerol with Ethanol (1 mg/ml)

205 mg of sodium hydroxide and 20 g of water for injection was added to a beaker (beaker A). The contents were stirred to dissolve the NAOH. 249 mg of vincristine sulfate and 2 ml of NaOH solution from beaker A were added into a 200 ml beaker (beaker B) and then 3 ml of dehydrated ethanol was added into beaker B and the contents stirred for 5 minutes to complete the reaction. The solution was white and turbid. 74.9 g (about 95 ml) of dehydrated ethanol was added into beaker B, the solution had no obvious change. After the solution is heated to approximately 25° C. 126.3 g (100 ml) of glycerin was then added into beaker B, after which the solution became clear, colorless and transparent. The pH of the solution was 7.26. A small amount of acetic acid was added into beaker B until the pH measured approximately 5.99. A small amount of ethanol was added into beaker B until the volume of the contents of beaker B reached 200 ml. The solution was passed through a 0.22 micron filter and then 4.2 ml of filtrate was filled into a vial under nitrogen. A stopper was inserted into the vial and then the vial was sealed with an aluminum cap. The average particle size of the water in oil emulsion was 115.2 nm.

Example 23: Bendamustine Base Formulation Comprising 80% of PEG and 20% of Ethanol 2000 mg of bendamustine base was added into a beaker of 200 ml size, 80 ml of $PEG_{300}$ and 20 ml of dehydrated ethanol was poured into the beaker with stirring. The experiment was conducted in a water bath at 25.0° C. The contents of the beaker were vibrated by ultrasound vibration for 10 minutes. The pH detected was 5.56. An additional amount of ethanol was added into the beaker until the volume of the contents of the beaker reached 100 ml. The solution was passed through a 0.22 micron filter and then 5.2 ml of filtrate was filled into a vial under nitrogen. A stopper was inserted into the vial and then the vial was sealed with an aluminum cap. The total related matter was 2.89% (limit less than 3.5%).

Example 24: Bendamustine Base Formulation Comprising 40% $PEG_{300}$ and Ethanol (5 mg/ml) Made from Bendamustine Hydrochloride 1216 mg of sodium hydroxide was added into a beaker (beaker A) of 50 ml size, then 5 ml of water for injection and 5 ml of dehydrated ethanol was added into beaker A. 1054 mg of bendamustine hydrochloride was put into a 100 ml beaker (beacher B) and then 3.5 ml of water for injection was added, after which the contents were stirred. The resulting was milky white, with un-dissolved particles at the bottom. 80 ml of $PEG_{300}$ was added into beaker B, after which the contents were stirred. The solution in beaker B turned into a light-yellow liquid. 1 ml of sodium hydroxide solution from beaker A was added into beaker B, and the pH tested was 5.96. 118 ml of dehydrated ethanol was poured into beaker B, the contents of which were stirred evenly. The resulting solution was clear and transparent. A small amount of dehydrated ethanol was added into beaker B until the volume reached 200 ml and the pH value of the solution tested was 6.05. The solution was then passed through a 0.22 micron filter and then 5.2 ml of filtrate was filled into a vial under nitrogen. A stopper was inserted into the vial and the vial was then sealed with an aluminum cap. The average particle size of the water in oil emulsion was 7.3 nm. The total related matter was 1.57% (limit less than 3.5%).

Example 25: Bendamustine Base Formulation Comprising 30% $PEG_{300}$ and Ethanol (15 mg/ml)

1553 mg of sodium hydroxide and 20 g of water for injection was added into a 100 ml beaker (beaker A), the contents of which were stirred until the NaOH was fully dissolved. 1582 mg of benzdamustine hydrochloride was added into a 200 ml beaker (beaker B). 2 ml of NaOH solution from beaker A and 3 ml of dehydrated ethanol were added into beaker B and the contents of beaker B were stirred. Another 48 ml of dehydrated ethanol was added into beaker B. The solution was milky white and turbid. 30 ml of $PEG_{300}$ was poured into beaker B, stirred evenly for 1.5 minutes. There was no obvious change in the appearance of the solution. 0.5 ml of sodium hydroxide solution was added into beaker B. Again, no obvious change in the appearance of the solution was noted.

1.035 g of acetic acid was added into beaker B. The pH of the solution at that time was 4.85. Another 1 ml of sodium hydroxide solution was added into beaker B. The pH detected was 6.35.

The solution was next placed in a water bath of 30° C. for 3 minutes. The solution became clear and transparent. The pH was 6.09. An addition amount of dehydrated ethanol was added to beaker B until the volume of the contents of beaker B reached 100 ml. The solution was passed through a 0.22 micron filter and then 2.2 ml of filtrate was filled into a vial under nitrogen. A stopper was inserted into the vial and then the vial was sealed with an aluminum cap. The total related matter was 1% (limit less than 3.5%). The average particle size of the water in oil emulsion was 10.7 nm.

Example 26: Bendamustine Base Formulation Comprising Oleic Acid and Ethanol (15 mg/ml)

1551 mg of sodium hydroxide and 20 ml water for injection were added into a 50 ml beaker (beaker A) and stirred to form a sodium hydroxide solution. 1583 mg of bendamustine hydrochloride was put in a 100 ml beaker (beaker B). 2 ml of sodium hydroxide solution from beaker A was transferred into beaker B, and then 10 ml of dehydrated ethanol was added into the beaker B after which the contents were stirred to complete the reaction.

Another 45 ml of dehydrated ethanol was added into beaker B and the contents of beaker B were stirred evenly. 40 ml of oleic acid was added into beaker B and the contents again were stirred. The pH tested was 5.0 An additional amount of dehydrated ethanol was added into beaker B until the volume of the contents of beaker B reached 100 ml. The solution was passed through a 0.22 micron filter and then 2.2 ml of filtrate was filled into a vial under nitrogen. A stopper was inserted into the vial and the vial was then sealed with an aluminum cap. The water detected was 3.77%, pH was 5.125. The total impurity was 0.355%. The average particle size of the water in oil emulsion was 13.6 nm.

Example 27: Bendamustine Base Formulation Comprising Glycerol and Ethanol (15 mg/ml)

3255 mg of sodium bicarbonate and 35 ml of water for injection was added into a 50 ml beaker (beaker A), after which the contents were stirred to form a solution. 1584 mg of bendamustine hydrochloride was put into a second beaker (beaker B).

3.5 ml of sodium bicarbonate solution from beaker A was transferred to beaker B, and then 10 ml of dehydrated ethanol was added into beaker B, after which the contents were stirred for about 3 to 4 minutes to complete the reaction. Another 35 ml of dehydrated ethanol was added into beaker B and the contents were stirred evenly. 50 ml of glycerol was added into beaker B and the contents were again stirred. 0.4 g of acetic acid and 2 ml of water was added into beaker B. The pH tested was 4.3. An additional amount of dehydrated ethanol was added into beaker B until the volume of the contents of beaker B reached 100 ml. The solution was passed through a 0.22 micron filter and then 2.2 ml of filtrate was filled into a vial under nitrogen. A stopper was inserted into the vial and then the vial was sealed with an aluminum cap. The water detected was 5.74%. The pH of the solution was 4.347% with total impurities of 0.826%. The average particle size of the water in oil emulsion was 11.7 nm.

Example 28: Mechlorethamine Base Formulation Comprising Median Chain Triglyceride and Ethanol 608 mg of mechlorethamine hydrochloride and 0.75 ml of water for injection was added into a 400 ml beaker (beaker A) and the contents were stirred. 2.6 ml of water, 1.98 ml of dehydrated ethanol and 1.26 g of sodium hydroxide, were added into a 50 ml beaker (beaker B), the contents of which were stirred to dissolve the NaOH completely. Next, 0.5 ml of the sodium hydroxide solution from beaker B was added into beaker A. The contents of beaker A were stirred to make the reaction complete.

100 ml of a median chain oil was added slowly to beaker A. Then 50 ml of dehydrated ethanol was added into beaker A and the contents of beaker A were stirred evenly. An amount of dehydrated ethanol was added into beaker A until the volume of the contents of beaker A reached 200 ml. The solution was then passed through a 0.22 micron filter after which 4.2 ml of filtrate was filled into a vial under nitrogen. A stopper was placed into the vial, after which the vial was sealed with an aluminum cap. The water content was 0.69%, the pH was 7.18 and the particle size of the solution was 2.1 nm. The total impurities of the solution were 1.91%.

Example 29: Mechlorethamine Base Formulation Comprising $PEG_{300}$ and Ethanol 609 mg of mechlorethamine hydrochloride and 0.75 ml of water for injection were added into a 400 ml beaker (beaker A) and then the contents were stirred. 2.5 ml of water and 1306 mg of sodium hydroxide, was added into a 50 ml beaker (beaker B) and the contents were stirred to dissolve the NaOH completely. Next, 0.25 ml of sodium hydroxide solution from beaker B and 5 ml of ethanol was added into beaker A. The contents of beaker A were stirred to complete the reaction. 100 ml of dehydrated ethanol and 80 ml of $PEG_{300}$ were added slowly to beaker A. The pH tested was 5.5. An additional amount of dehydrated ethanol was added into beaker A until the volume of the contents of beaker A reached 200 ml. The solution was passed through a 0.22 micron filter and then 4.2 ml of filtrate was filled into a vial under nitrogen. A stopper was inserted into the vial and then the vial was sealed with an aluminum cap. The water content was 0.6%, the pH was 5.74 and the particle size of the solution was 2.2 nm.

Example 30: Vindesine Base Formulation Comprising 50% Glycerol with Ethanol (0.5 mg/ml)

96 mg of sodium hydroxide and 9.99 g of water for injection was added to a beaker of 20 ml size (beaker A). The contents were stirred to dissolve the NAOH. 102 mg of vindesine sulfate and 1 ml of NaOH solution from beaker A were added into a 400 ml beaker (beaker B), then 3 ml of dehydrated ethanol was added into beaker B, after which the contents of beaker B were stirred for 5 minutes to complete the reaction. The resulting solution was white and turbid. 95 ml of dehydrated ethanol was added into beaker B.

100 ml of glycerin was added into beaker B and the solution was stirred. The solution then became clear, colorless and transparent after stirring. The temperature of the beaker was kept at 22° C. The pH of the solution tested was 6.59. A small amount of acetic acid was then added into beaker B. The pH tested was 5.22. A small amount of ethanol was added into beaker B until the volume of the contents of beaker B reached 200 ml. The solution was passed through a 0.22 micron filter and then 4.2 ml of filtrate was filled into a vial under nitrogen. A stopper was inserted into the vial and then the vial was sealed with an aluminum cap. The water content was 0.6%, the pH was 5.99 and the particle size of the solution was 21.4 nm. The total impurities were 1.53%.

Example 31: Vindesine Base Formulation Comprising a Median Chain Triglyceride with Ethanol 96 mg of sodium hydroxide and 9.987 g of water for injection were added into a beaker of 20 ml size (beaker A). The contents were stirred to dissolve the NAOH.

103 mg of vindesine sulfate and 1 ml of NaOH solution from beaker A were added into a 400 ml beaker (B), then 3 ml of dehydrated ethanol was added into beaker B, and the contents of beaker B were stirred for 5 minutes to complete the reaction. The resulting solution was white and turbid.

100 ml of dehydrated ethanol was added into beaker B. 80 ml of a median chain triglyceride was added into the beaker B and the solution was stirred. The solution became a clear, pale yellow and transparent after stirring. The temperature of the beaker was kept at 30° C.

The pH of the solution tested was 6.55. A small amount of ethanol was added into beaker B until the volume of the contents of beaker B reached 200 ml. The solution was passed through a 0.22 micron filter and then 4.2 ml of filtrate was filled into a vial under nitrogen. A stopper was inserted into the vial and then the vial was sealed with an aluminum cap. The average particle size of the water in oil emulsion was 11.7 NM. The water content was 0.69%. The total impurities were 1.55%.

Example 32: Vindesine Base Formulation Comprising Oleic Acid with Ethanol (0.5 mg/ml)

96 mg of sodium hydroxide and 10.018 g of water for injection were added into a beaker of 20 ml size (beaker A). The contents were stirred to dissolve the NAOH. 102 mg of vindesine sulfate and 1 ml of NaOH solution from beaker A were added into a 400 ml beaker (beaker B) and then 3 ml of dehydrated ethanol was added into beaker B, after which the contents were stirred for 5 minutes to complete the reaction. The resulting solution was white and turbid. 100 ml of dehydrated ethanol was added into beaker B.

80 ml of oleic acid was then added into beaker B and the solution stirred. The resulting solution became clear, pale yellow and transparent after stirring. The temperature of the beaker was kept at 30° C. The pH of the solution tested was 4.66. A small amount of ethanol was added into beaker B until the volume of the contents of beaker B reached 200 ml. The solution was then passed through a 0.22 micron filter and 4.2 ml of filtrate was filled into a vial under nitrogen. A stopper was inserted in the vial and then the vial was sealed with an aluminum cap. The average particle size of the water in oil emulsion was 20.6 nm. The water content was 0.67% and the pH was 5.029. The total impurities were 1.55%.

Example 33: Doxorubicin Base Formulation Comprising 40% Oleic Acid/Ethanol (5 mg/ml)

514 mg of doxorubicin hydrochloride and 4.5 ml of water for injection was added into a 300 ml beaker (beaker A) and the contents were then stirred. 5.01 ml of water for injection and 726 mg of sodium acetate were added into a 20 ml beaker (beaker B) and stirred. 0.5 ml of sodium acetate solution from beaker B and 10 ml of dehydrated ethanol were transferred to beaker A and then stirred. 40 ml of dehydrated ethanol and 40 ml of oleic acid were added into beaker A. The pH tested was 4.74. 4.5 ml of sodium acetate solution from beaker B was added into beaker A. An additional amount of ethanol was added into the beaker A until the volume of the contents of beaker A reached 100 ml. The resultant solution was passed through a 0.22-micron filter while applying nitrogen and then 2.2 ml of filtrate was filled into a vial. A stopper was inserted into the vial and the vial was sealed with an aluminum cap under nitrogen. The assay was 97%, the pH was 5.07, the water content was 9.5% and the total related matter was 2.47%. The particle size was 37.4 nm.

CONCLUSION

In the preceding specification, the invention has been described with reference to specific exemplary embodiments and examples thereof. It will, however, be evident that various modifications and changes may be made thereto without departing from the broader spirit and scope of the invention as set forth in the claims that follow. It will also be apparent to those skilled in the art that the local anticancer formulations of the present invention may be changed in additional ways or utilized in many additional presurgical conditions, during surgical and post-surgical treatments not specifically mentioned herein. Additionally, it is contemplated that such formulations may be utilized at additional sites not specifically mentioned herein (including topically). Such obvious modifications are considered to be within the scope of the appended claims. The Specification is accordingly to be regarded in an illustrative manner rather than a restrictive sense.

What is claimed:

1. An intratumor injectable formulation consisting of comprising a basic chemotherapeutic drug selected from the group consisting of an anthracycline base, a vinca alkaloid base, eribulin base and an alkylating agent base, or a pharmaceutically acceptable salt thereof, and a pharmaceutically acceptable biocompatible carrier for injection of the drug selected from the group consisting of a PEG of molecular weight of 200 to 400, an oleic acid, a liquid alcohol selected from the group consisting of ethanol, benzyl alcohol, and mixtures thereof, a glycerin, and mixtures thereof, and an organic acid selected from the group consisting of acetic acid, malic acid, fumaric acid, tartaric acid, succinic acid, maleic acid, and mixtures thereof, wherein the intratumor injectable formulation is a solution and contains more than 4% to less than 15% of water by volume, and optionally containing sodium or potassium chloride.

2. The intratumor injectable formulation of claim 1, wherein the pharmaceutically acceptable biocompatible carrier for injection is an organic liquid selected from the group consisting of a PEG of molecular weight of 200 to 400, oleic acid, glycerol, a liquid alcohol comprising ethanol and benzyl alcohol, and mixtures thereof, such that the formulation is a solution.

3. The intratumor injectable formulation of claim 1, wherein the basic chemotherapeutic drug is a desalinated salt form of a chemotherapeutic drug, wherein the biocompatible carrier is selected from the group consisting of a PEG of molecular weight of 200 to 400, a medium chain triglyceride, oleic acid, glycerol, a liquid alcohol comprising ethanol and benzyl alcohol, and combinations thereof, and a salt selected from the group consisting of sulfate, chloride, mesylate and mixtures thereof, such that the formulation is a solution.

4. The intratumor injectable formulation of claim 1, wherein the vinca alkaloid base is selected from the group consisting of vinblastine, vincristine, vindesine, and mixtures thereof; wherein the anthracycline base is selected from the group consisting of doxorubicin, epirubicin, daunorubicin, mitoxantrone, idarubicin, amrubicin, aclarubicin, valrubicin, and mixtures thereof; and wherein the alkylating agent base is selected from the group consisting of bendamustine, mechlorethamine, procarbazine, and mixtures thereof.

5. The intratumor injectable formulation of claim 3, wherein the injectable formulation is the basic chemotherapeutic agent, the biocompatible carrier, an alcohol comprised of ethanol or benzyl alcohol, sodium or potassium chloride, an organic acid and wherein the organic acid is selected from the group consisting of acetic acid, malic acid, fumaric acid, tartaric acid, succinic acid, maleic acid, and mixtures thereof, and wherein the water is less than 15% of the injectable formulation and the amount of organic solvent is more than 85% of the volume of the solution.

6. The intratumor injectable formulation of claim 1, wherein the injectable formulation is a solution comprising an anthracycline base selected from the group consisting of doxorubicin base, epirubicin base, daunorubicin base, amrubicin base and mitoxantrone base, an oleic acid, glycerol, acetic acid, more than 4% to less than 15% of water by volume of the solution and the liquid alcohol.

7. The intratumor injectable formulation of claim 1, wherein the formulation is a solution comprising daunorubicin base, oleic acid, ethanol, acetic acid, sodium or potassium chloride and from about 4% to about 10% of water by volume of the emulsion.

8. The intratumor injectable formulation of claim 1, wherein the formulation is a solution comprising amrubicin base, oleic acid, ethanol, acetic acid, sodium or potassium chloride and from about 4% to about 10% of water by volume of the solution.

9. The intratumor injectable formulation of claim 1, wherein the formulation is a solution comprising mitoxantrone base, oleic acid, glycerol, ethanol, acetic acid, sodium or potassium chloride and from about 2% to about 10% of water by volume of the solution.

10. The intratumor injectable formulation of claim 1, wherein the formulation comprises mitoxantrone base, ethanol and acetic acid, and further includes either oleic acid or glycerol, wherein the formulation is a solution.

11. The intratumor injectable formulation of claim 1, wherein the formulation is a solution comprising doxorubicin base, oleic acid, ethanol, acetic acid, NaCl and from about 4% to about 15% of water by volume of the solution.

12. The intratumor injectable formulation of claim 1, wherein the formulation is a solution comprising the basic chemotherapeutic agent, oleic acid, an alcohol, acetic acid, sulfate or chloride, and from about 4% to about 15% of water by volume of the solution, wherein the basic chemotherapeutic agent selected from the group consisting of daunorubicin base, epirubicin base, doxorubicin base, mitoxantrone base and amrubicin base.

13. The intratumor injectable formulation of claim 1, wherein the basic chemotherapeutic drug is selected from the group consisting of a vincristine base, a vinblastine base and a vindesine base wherein the biocompatible carrier is a mixture of a liquid alcohol comprising ethanol or benzyl alcohol, glycerol or oleic acid, and wherein the formulation further comprises acetic acid, sulfate or chloride salt, such that the formulation is a solution containing from about 0.5% to about 5% of water by volume of the solution.

14. The intratumor injectable formulation of claim 1, wherein the basic chemotherapeutic drug comprises bendamustine base and the pharmaceutically acceptable biocompatible carrier is a mixture selected from the group consisting of ethanol mixed with a PEG of molecular weight from about 200 to 400 or oleic acid mixed with acetic acid, such that the formulation is a solution.

15. The intratumor injectable formulation of claim 1, wherein the basic chemotherapeutic drug formulation is a solution comprises bendamustine base and wherein the pharmaceutically acceptable biocompatible carrier is a mixture of oleic acid and an ethanol, the formulation further comprises a water phase of acetic acid, sodium or potassium chloride and from about 2% to about 10% of water by volume of the solution.

16. The intratumor injectable formulation of claim 1, wherein the basic chemotherapeutic drug formulation is a solution comprises bendamustine base and wherein the pharmaceutically acceptable biocompatible carrier is a mixture of glycerol and an ethanol, the formulation further comprising a water phase of acetic acid, sodium or potassium chloride and a small amount of water from about 2% to about 10% of water by volume of the solution.

17. The intratumor injectable formulation of claim 1, wherein the formulation is a solution comprising bendamustine base dissolved in a mixture of a PEG of molecular weight of 200 to 400 and an ethanol, acetic acid, sodium or potassium chloride and from about 2% to about 10% of water by volume of the solution.

18. The intratumor injectable formulation of claim 1, wherein the basic chemotherapeutic drug comprises mechlorethamine base and and ethanol, the formulation further comprising acetic acid, and less than about 10% of water by volume of the formulation, such that the formulation is a solution.

19. The intratumor injectable formulation of claim 1, wherein the basic chemotherapeutic drug comprises mechlorethamine base and the pharmaceutically acceptable biocompatible carrier comprises ethanol, the formulation further comprising acetic acid, sodium or potassium chloride and less than about 10% of water by volume of the formulation, such that the formulation is a solution.

20. The intratumor injectable formulation of claim 1, wherein the basic chemotherapeutic drug is eribulin base, wherein the biocompatible carrier is a mixture of ethanol or benzyl alcohol and, glycerol, PEG of molecular weight 200 to 400 or oleic acid, and wherein the formulation further comprises a water phase of acetic acid, sodium mesylate or potassium mesylate and water such that the formulation is a solution.

21. An intratumor injectable formulation kit, comprising a first vial containing a basic chemotherapeutic drug and a second vial containing a pharmaceutically acceptable excipient for delivery of the drug into a tumor, the pharmaceutically acceptable excipient comprising a solvent selected from the group consisting of a PEG, an oleic acid, glycerin, a liquid alcohol selected from the group consisting of ethanol, benzyl alcohol, and mixtures thereof, and mixtures thereof, an organic acid selected from the group consisting of acetic acid, malic acid, fumaric acid, tartaric acid, succinic acid, maleic acid, and mixtures thereof, a pharmaceutically acceptable diluent, and mixtures thereof, wherein the PEG has a molecular weight from about PEG200 to about PEG400, wherein the formulation in the first vial is a solution and contains more than 4% to less than 15% of water by volume; and wherein the basic chemotherapeutic drug is selected from the group consisting of an anthracycline base, a vinca alkaloid base, eribulin base and an alkylating agent base.

22. The intratumor injectable formulation kit of claim 21, wherein the anthracycline base is selected from the group consisting of doxorubicin base, epirubicin base, amrubicin base, daunorubicin base and mitoxantrone base, and wherein the pharmaceutical acceptable excipient comprises a mixture of ethanol and oleic acid or PEG, or glycerol.

23. The intratumor injectable formulation of claim 21, wherein the pharmaceutically acceptable biocompatible carrier for injection comprises an alcohol selected from the group consisting of ethanol, benzyl alcohol and combinations thereof.

24. A method of treating a malignant mass in a mammal, comprising administering the intratumor injectable formulation of claim 1 directly into the malignant mass, wherein the malignant mass is a primary or secondary tumor located in skin, eye, tongue, mouth, thyroid, breast, cervix, uterus, anus, prostate, vagina, bone, urinary bladder, ureter, urethra, penis, testis, epididymis, nasopharynx, liver, kidney, gall bladder, ovary, oviduct, pancreas, metastasis of lymph node, peritoneum metastasis of the abdominal cavity, esophagus, stomach, duodenum, small intestine, large intestine, caecum, rectum, lung, trachea, larynx, brain, a malignant lymphoma or lymph node metastasis, metastatic breast cancer, metastatic Wilms' tumor, Kaposi's sarcoma, metastatic neuroblastoma or a metastatic soft tissue sarcoma.

25. A method of making an intratumor injectable formulation of claim 1 comprising dissolving a basic chemotherapeutic drug selected from the group consisting of an anthracycline base, a vinca alkaloid base, eribulin base or an alkylating agent base in an organic liquid comprising a solvent selected from the group consisting of a PEG of molecular weight of 200 to 400, oleic acid, glycerol, a liquid alcohol and mixtures thereof.

* * * * *